US008942776B2

(12) United States Patent
LeBoeuf et al.

(10) Patent No.: US 8,942,776 B2
(45) Date of Patent: *Jan. 27, 2015

(54) PHYSIOLOGICAL MONITORING METHODS

(71) Applicant: Valencell, Inc., Raleigh, NC (US)

(72) Inventors: Steven Francis LeBoeuf, Raleigh, NC (US); Jesse Berkley Tucker, Knightdale, NC (US); Michael Edward Aumer, Raleigh, NC (US); Steven Matthew Just, Cary, NC (US)

(73) Assignee: Valencell, Inc., Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/298,219

(22) Filed: Jun. 6, 2014

(65) Prior Publication Data
US 2014/0288394 A1    Sep. 25, 2014

Related U.S. Application Data

(63) Continuation of application No. 13/715,247, filed on Dec. 14, 2012, now Pat. No. 8,788,002, which is a continuation-in-part of application No. 12/691,388, filed on Jan. 21, 2010, now Pat. No. 8,700,111.

(Continued)

(51) Int. Cl.
*A61B 5/00* (2006.01)
*H04R 1/10* (2006.01)
(Continued)

(52) U.S. Cl.
CPC ............. *A61B 5/6817* (2013.01); *A61B 5/0077* (2013.01); *A61B 5/6815* (2013.01); *H04R 1/1091* (2013.01); *A61B 5/6835* (2013.01);
(Continued)

(58) Field of Classification Search
USPC .......................................................... 600/310
See application file for complete search history.

(56) References Cited

U.S. PATENT DOCUMENTS 5,086,229 A    2/1992  Rosenthal et al.
5,596,987 A    1/1997  Chance
(Continued)

FOREIGN PATENT DOCUMENTS

EP    2 077 091 A2    7/2009
JP    7-241279    9/1995
(Continued)

OTHER PUBLICATIONS

Fitrainer "The Only Trainer You Need"; http://itami.com; Downloaded Feb. 26, 2010; © 2008 FiTrianer™; 2 pages.

*Primary Examiner* — Rodney Fuller
(74) *Attorney, Agent, or Firm* — Myers Bigel Sibley & Sajovec

(57) ABSTRACT

A method of monitoring a subject includes attaching a sensor module having at least one optical emitter and detector to a body of the subject, delivering light from the at least one optical emitter into the body of the subject via a first light guide that is in optical communication with the at least one optical emitter, and collecting light from the body of the subject via a second light guide that is in optical communication with the at least one optical detector. The first light guide has a proximal end optically coupled to the at least one optical emitter and delivers light from the at least one optical emitter via a distal end thereof. The second light guide has a proximal end optically coupled to the at least one optical detector and collects light from the body of the subject via the distal end thereof.

18 Claims, 28 Drawing Sheets

Related U.S. Application Data

(60) Provisional application No. 61/208,567, filed on Feb. 25, 2009, provisional application No. 61/208,574, filed on Feb. 25, 2009, provisional application No. 61/212,444, filed on Apr. 13, 2009, provisional application No. 61/274,191, filed on Aug. 14, 2009.

(51) Int. Cl.
*A61B 5/0205* (2006.01)
*A61B 5/11* (2006.01)
*A61B 5/024* (2006.01)
*A61B 5/08* (2006.01)

(52) U.S. Cl.
CPC ............ *A61B 5/0059* (2013.01); *A61B 5/0082* (2013.01); *A61B 5/0205* (2013.01); *A61B 5/11* (2013.01); *A61B 5/6803* (2013.01); *A61B 5/681* (2013.01); *A61B 5/0084* (2013.01); *A61B 5/721* (2013.01); *A61B 5/7225* (2013.01); *A61B 5/02427* (2013.01); *A61B 5/0816* (2013.01)
USPC ........................................................ 600/310

(56) References Cited

U.S. PATENT DOCUMENTS

| | | | |
|---|---|---|---|
| 6,078,829 A | 6/2000 | Uchida et al. | |
| 6,080,110 A | 6/2000 | Thorgersen | |
| 6,358,216 B1* | 3/2002 | Kraus et al. | 600/549 |
| 6,371,925 B1 | 4/2002 | Imai et al. | |
| 6,783,501 B2 | 8/2004 | Takahashi et al. | |
| 6,808,473 B2 | 10/2004 | Hisano et al. | |
| 6,859,658 B1 | 2/2005 | Krug | |
| 7,107,088 B2* | 9/2006 | Aceti | 600/340 |
| 7,209,775 B2 | 4/2007 | Bae et al. | |
| 8,055,319 B2 | 11/2011 | Oh et al. | |
| 8,251,903 B2 | 8/2012 | Leboeuf et al. | |
| 8,512,242 B2 | 8/2013 | Leboeuf et al. | |
| 2002/0091049 A1 | 7/2002 | Hisano et al. | |
| 2003/0109030 A1* | 6/2003 | Uchida et al. | 435/287.1 |
| 2004/0034293 A1 | 2/2004 | Kimball | |
| 2004/0054291 A1 | 3/2004 | Schulz et al. | |
| 2004/0225207 A1 | 11/2004 | Bae et al. | |
| 2005/0043600 A1 | 2/2005 | Diab et al. | |
| 2005/0177034 A1 | 8/2005 | Beaumont | |
| 2005/0209516 A1 | 9/2005 | Fraden | |
| 2005/0228299 A1 | 10/2005 | Banet | |
| 2006/0009685 A1 | 1/2006 | Finarov et al. | |
| 2008/0076972 A1 | 3/2008 | Dorogusker et al. | |
| 2008/0096726 A1 | 4/2008 | Riley et al. | |
| 2008/0165017 A1 | 7/2008 | Schwartz | |
| 2008/0177162 A1 | 7/2008 | Bae et al. | |
| 2009/0030350 A1 | 1/2009 | Yang et al. | |
| 2009/0054752 A1 | 2/2009 | Jonnalagadda et al. | |
| 2009/0105556 A1 | 4/2009 | Fricke et al. | |
| 2009/0270698 A1 | 10/2009 | Shioi et al. | |
| 2009/0287067 A1 | 11/2009 | Dorogusker et al. | |
| 2010/0168531 A1 | 7/2010 | Shaltis et al. | |
| 2010/0217103 A1 | 8/2010 | Abdul-Hafiz et al. | |
| 2010/0298653 A1 | 11/2010 | McCombie et al. | |
| 2011/0105869 A1 | 5/2011 | Wilson et al. | |
| 2012/0179011 A1 | 7/2012 | Moon et al. | |
| 2012/0197093 A1 | 8/2012 | LeBoeuf et al. | |
| 2013/0131519 A1 | 5/2013 | LeBoeuf et al. | |

FOREIGN PATENT DOCUMENTS

| | | |
|---|---|---|
| JP | 9-253062 | 9/1997 |
| JP | 9-299342 | 11/1997 |
| JP | 2000-116611 | 4/2000 |
| JP | 2001-25462 | 1/2001 |
| JP | 2007-185348 | 7/2007 |
| WO | WO 2013/038296 A1 | 3/2013 |

* cited by examiner

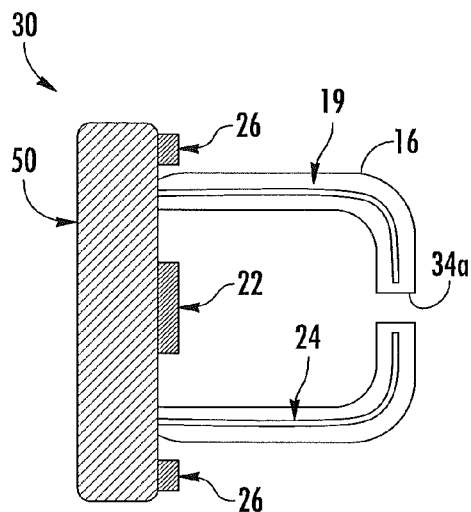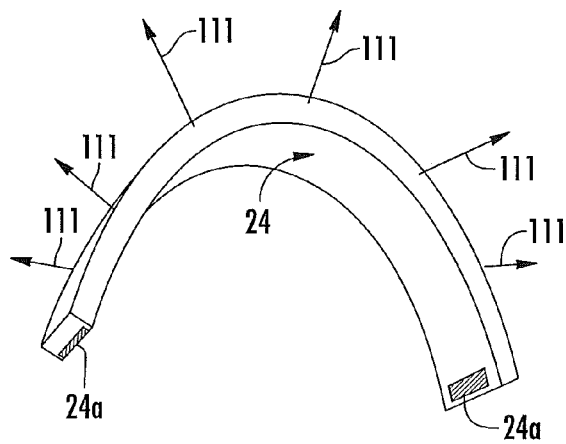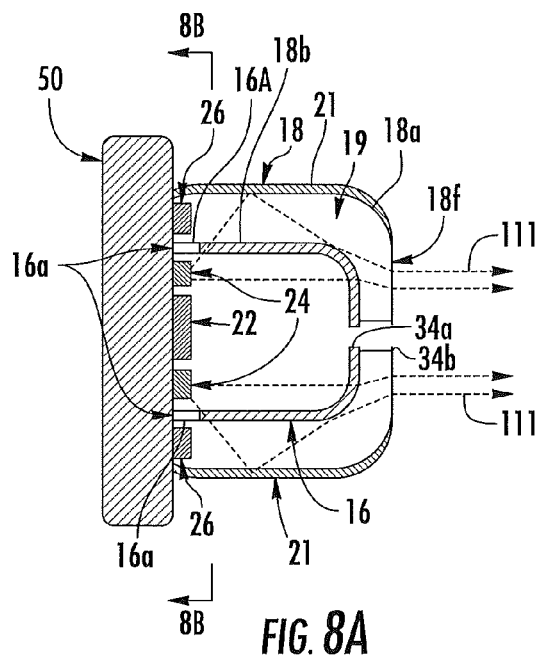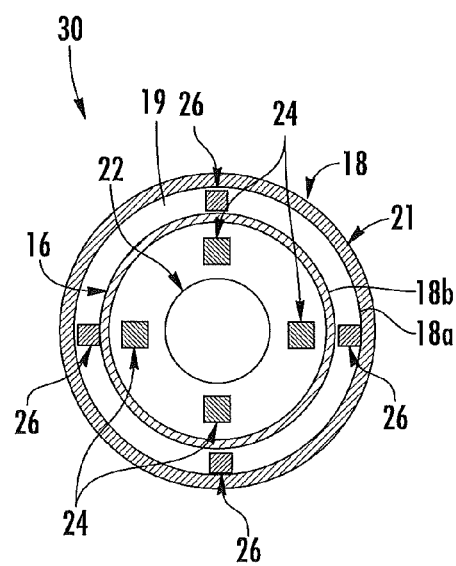

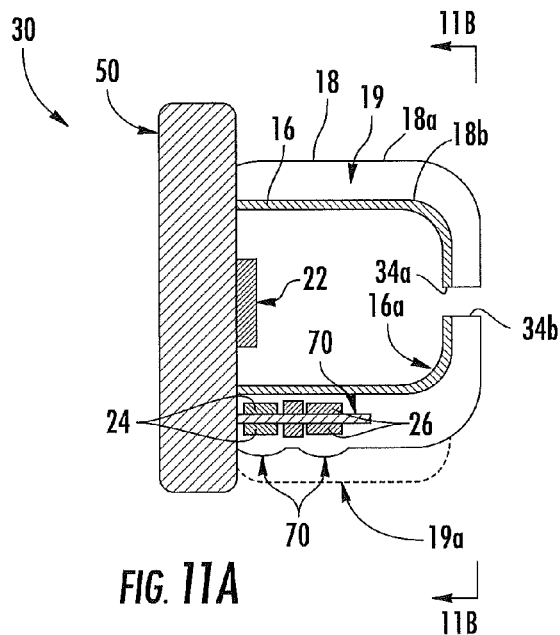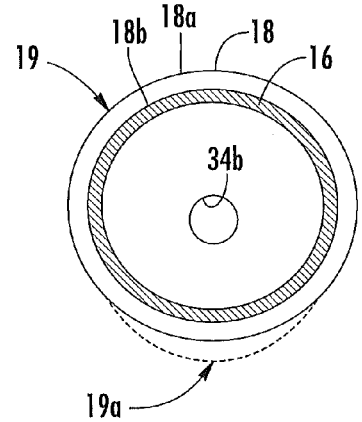
FIG. 11A  FIG. 11B
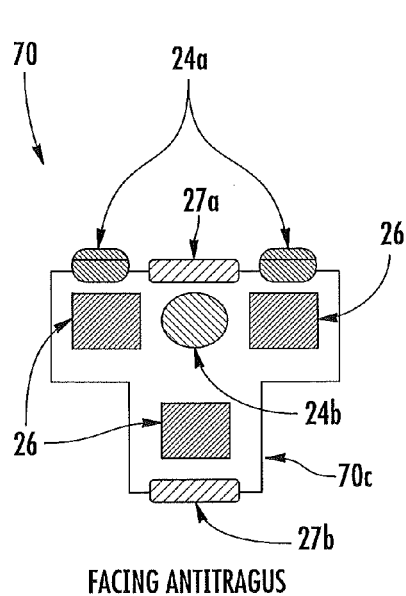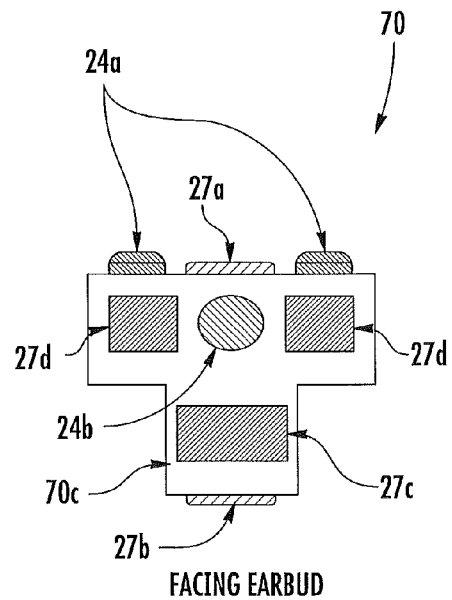
FIG. 12A  FIG. 12B

| STEPS | PACE | ACTIVITY INTENSITY | DATA INTEGRITY | BLOOD FLOW | HEART RATE | BREATHING RATE | BLOOD PRESSURE | BLOOD ANALYTE LEVELS | ... |

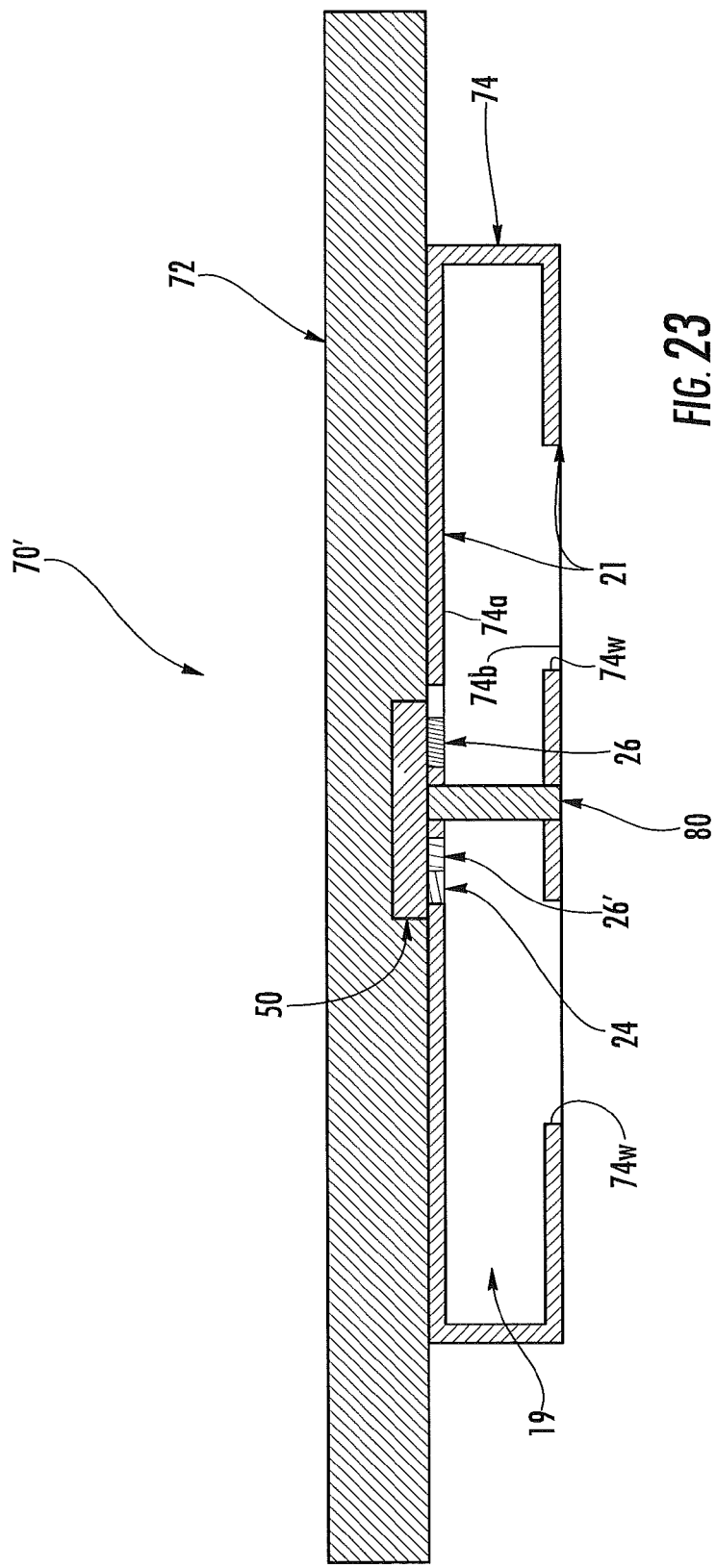

SEE FIG. 38

PHYSIOLOGICAL MONITORING METHODS

RELATED APPLICATIONS

This application is a continuation application of U.S. patent application Ser. No. 13/715,247, filed Dec. 14, 2012, which is a continuation-in-part of U.S. patent application Ser. No. 12/691,388, filed Jan. 21, 2010, now U.S. Pat. No. 8,700,111, which claims the benefit of and priority to U.S. Provisional Patent Application No. 61/208,567 filed Feb. 25, 2009, U.S. Provisional Patent Application No. 61/208,574 filed Feb. 25, 2009, U.S. Provisional Patent Application No. 61/212,444 filed Apr. 13, 2009, and U.S. Provisional Patent Application No. 61/274,191 filed Aug. 14, 2009, the disclosures of which are incorporated herein by reference as if set forth in their entireties.

FIELD OF THE INVENTION

The present invention relates generally to headsets and, more particularly, to headset earbuds.

BACKGROUND OF THE INVENTION

There is growing market demand for personal health and environmental monitors, for example, for gauging overall health and metabolism during exercise, athletic training, dieting, daily life activities, sickness, and physical therapy. However, traditional health monitors and environmental monitors may be bulky, rigid, and uncomfortable—generally not suitable for use during daily physical activity. There is also growing interest in generating and comparing health and environmental exposure statistics of the general public and particular demographic groups. For example, collective statistics may enable the healthcare industry and medical community to direct healthcare resources to where they are most highly valued. However, methods of collecting these statistics may be expensive and laborious, often utilizing human-based recording/analysis steps at multiple sites.

As such, improved ways of collecting, storing and analyzing physiological information are needed. In addition, improved ways of seamlessly extracting physiological information from a person during everyday life activities, especially during high activity levels, may be important for enhancing fitness training and healthcare quality, promoting and facilitating prevention, and reducing healthcare costs.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a headset configured to be attached to the ear of a person includes a base, an earbud housing extending outwardly from the base that is configured to be positioned within an ear of a subject, and a cover surrounding the earbud housing. The base includes a speaker, an optical emitter, and an optical detector. The cover includes light transmissive material that is in optical communication with the optical emitter and the optical detector and serves as a light guide to deliver light from the optical emitter into the ear canal of the subject wearing the headset at one or more predetermined locations and to collect light external to the earbud housing and deliver the collected light to the optical detector. The optical emitter, via the light-guiding cover, directs optical energy towards a particular region of ear and the optical detector detects secondary optical energy emanating from the ear region. In some embodiments, the optical detector may include an optical filter configured to pass secondary optical energy at selective wavelengths. In some embodiments, the light transmissive material of the cover may be configured, for example via the use of cladding and/or light reflective material, such that the cover serves as a light guide that is coupled in parallel to the optical emitter and detector. In some embodiments, the light transmissive material of the cover may be configured, for example via the use of cladding and/or light reflective material, such that the cover serves as a light guide that is coupled perpendicular to the optical emitter and detector.

In some embodiments, the headset may include various electronic components secured to the base. For example, the headset may include one or more environmental sensors configured to detect and/or measure environmental conditions in a vicinity of the headset. The headset may include a signal processor configured to receive and process signals produced by the optical detector. For example, in some embodiments, a signal processor may be configured to extract secondary optical energy and remove optical noise or environmental noise. The headset may include a signal processor configured to receive and process signals produced by the one or more environmental sensors. In addition, the headset may include a transmitter configured to transmit signals processed by the signal processor to a remote device in real time. Headsets according to embodiments of the present invention may utilize, for example, Bluetooth®, Wi-Fi, ZigBee, or other wireless transmitters.

In some embodiments, a housing is secured to and overlies the base so as to enclose and protect the speaker, optical emitter and optical detector, as well as other electronic components secured to the base (e.g., sensors, processor, transmitter etc.).

The earbud housing is in acoustical communication with the speaker and has at least one aperture through which sound from the speaker can pass. The light-guiding cover surrounding the earbud housing also includes at least one aperture through which sound from the speaker can pass. The cover may be formed from a soft, resilient material, such as silicone which deforms when inserted within an ear canal of a subject. In some embodiments, the cover includes an alignment member that facilitates alignment of the earbud housing within an ear canal of a subject.

Light directed into the ear of a subject from a light emitter and the subsequent collection of light at a light detector, according to embodiments of the present invention, may be utilized for detecting and/or measuring, among other things, body temperature, skin temperature, blood gas levels, muscle tension, heart rate, blood flow, cardiopulmonary functions, etc.

In some embodiments of the present invention, the light-guiding cover may include a lens that is in optical communication with the optical emitter and/or optical detector. The lens may be configured to focus light emitted by the optical emitter and/or to focus collected light toward the optical detector. In some embodiments, multiple lenses may be incorporated into a light-guiding cover.

In some embodiments, the light-guiding cover may include a light diffusion region in optical communication with the light transmissive material that diffuses light emitted by the optical detector.

In some embodiments, the light-guiding cover may include a luminescence-generating region, such as a phosphor-containing region, that is in optical communication with the light transmissive material. The luminescence-generating region may be embedded within the light-guiding cover and/or on a surface of the light-guiding cover. The luminescence-generating region is configured to receive light emitted by the optical emitter and convert at least a portion of the received light to light having a different wavelength from that of the received light.

In some embodiments, the light-guiding cover includes one or more grooves formed therein. Each groove is configured to direct external light to the optical detector.

In some embodiments, the light transmissive material of the light-guiding cover is configured to direct light from the optical emitter to a plurality of locations at an outer surface of the cover for delivery into an ear canal of a subject.

In some embodiments, the light transmissive material of the light-guiding cover is a translucent material or includes translucent material in selected locations.

In some embodiments, a light reflective material is on at least a portion of one or both of the inner and outer surfaces of the light-guiding cover.

According to some embodiments of the present invention, a light-guiding earbud for a headset includes light transmissive material that is in optical communication with an optical emitter and optical detector associated with the headset. The light transmissive material is configured to deliver light from the optical emitter into the ear canal of a subject at one or more predetermined locations and to collect light external to the earbud housing and deliver the collected light to the optical detector. In some embodiments, the light emitter and light detector may be integral with the earbud. For example, in some embodiments, a flexible optical emitter is incorporated within the earbud and is in optical communication with the light transmissive material.

In some embodiments, an earbud includes at least one lens in optical communication with the light transmissive material. Each lens may be configured to focus light from the optical emitter onto one or more predetermined locations in the ear of a subject and/or to focus collected external light onto the optical detector.

In some embodiments of the present invention, an earbud may include luminescent material. Luminescent light is generated from optical excitation of the luminescent material by an optical emitter.

In some embodiments of the present invention, an earbud may integrate a sensor module containing a plurality of sensor elements for measuring physiological information and at least one noise source for measuring noise information. A "noise source", as used herein, refers to a sensor, such as an optical sensor, inertial sensor, electrically conductive sensor, capacitive sensor, inductive sensor, etc., and derives it name from the fact that it is a source of input to a filter, such as an adaptive filter described below.

The physiological sensors of the sensor module may generate a signal that includes physiological information plus noise information. The noise may be removed by combining the physiological information and noise information from the sensor module with noise information from the noise source of the sensor module via an electronic filtering method, such as a signal processing technique. Specific examples of such signal processing techniques include FIR (Finite Impulse Response), IIR (Infinite Impulse Response), informatics, machine learning, and adaptive filter methods. The output of the adaptive filter may be a physiological signal that is wholly or partially free of noise. In some embodiments, motion-related noise from a subject activity such as running may be removed from the physiological plus noise signal generated by a photoplethysmography (PPG) sensor for measuring blood constituent levels or blood flow properties, such as blood oxygen level, $VO_2$, or heart rate.

In some embodiments of the present invention, the noise source input of an adaptive filter may include a "blocked channel" of optical energy, an inertial sensor, or environmental energy. In some embodiments, the environmental energy may be unwanted ambient optical noise.

In some embodiments of the present invention, a processor/multiplexor processes physiological signals and noise signals into a data string. This data string may contain information relating to physiological information and motion-related information. The processing method may include signal processing techniques such as pre-adaptive signal conditioning, adaptive filtering, and parameter extraction.

In some embodiments, an earbud includes one or more sensor modules that includes one or more sensors for sensing physiological information and environmental information, such as noise, for example. As such, the earbud may function as a physiological monitor as well as an environmental monitor. In some embodiments, the earbud may include a microprocessor that is in electrical communication with the sensor module(s). For example, a microprocessor incorporated into an earbud may be configured to execute an adaptive filter algorithm to remove noise from at least one signal generated by a sensor module in the earbud. A microprocessor may also be configured to process information from the one or more sensors to generate a digital output string, wherein the digital output string includes a plurality of physiological and motion-related information.

Physiological sensors that may be incorporated into headsets and/or earbuds, according to some embodiments of the present invention, may be configured to detect and/or measure one or more of the following types of physiological information: heart rate, pulse rate, breathing rate, blood flow, $VO_2$, $VO_2$max, heartbeat signatures, cardio-pulmonary health, organ health, metabolism, electrolyte type and/or concentration, physical activity, caloric intake, caloric metabolism, blood metabolite levels or ratios, blood pH level, physical and/or psychological stress levels and/or stress level indicators, drug dosage and/or dosimetry, physiological drug reactions, drug chemistry, biochemistry, position and/or balance, body strain, neurological functioning, brain activity, brain waves, blood pressure, cranial pressure, hydration level, auscultatory information, auscultatory signals associated with pregnancy, physiological response to infection, skin and/or core body temperature, eye muscle movement, blood volume, inhaled and/or exhaled breath volume, physical exertion, exhaled breath physical and/or chemical composition, the presence and/or identity and/or concentration of viruses and/or bacteria, foreign matter in the body, internal toxins, heavy metals in the body, anxiety, fertility, ovulation, sex hormones, psychological mood, sleep patterns, hunger and/or thirst, hormone type and/or concentration, cholesterol, lipids, blood panel, bone density, organ and/or body weight, reflex response, sexual arousal, mental and/or physical alertness, sleepiness, auscultatory information, response to external stimuli, swallowing volume, swallowing rate, sickness, voice characteristics, voice tone, voice pitch, voice volume, vital signs, head tilt, allergic reactions, inflammation response, auto-immune response, mutagenic response, DNA, proteins, protein levels in the blood, water content of the blood, pheromones, internal body sounds, digestive system functioning, cellular regeneration response, healing response, stem cell regeneration response, etc.

Environmental sensors that may be incorporated into headsets and/or earbuds, according to some embodiments of the present invention, may be configured to detect and/or measure one or more of the following types of environmental information: climate, humidity, temperature, pressure, barometric pressure, soot density, airborne particle density, airborne particle size, airborne particle shape, airborne particle identity, volatile organic chemicals (VOCs), hydrocarbons, polycyclic aromatic hydrocarbons (PAHs), carcinogens, toxins, electromagnetic energy, optical radiation, X-rays, gamma rays, microwave radiation, terahertz radiation, ultraviolet radiation, infrared radiation, radio waves, atomic energy alpha particles, atomic energy beta-particles, gravity, light intensity, light frequency, light flicker, light phase, ozone, carbon monoxide, carbon dioxide, nitrous oxide, sulfides, airborne pollution, foreign material in the air, viruses, bacteria, signatures from chemical weapons, wind, air turbulence, sound and/or acoustical energy, ultrasonic energy, noise pollution, human voices, animal sounds, diseases expelled from others, exhaled breath and/or breath constituents of others, toxins from others, pheromones from others, industrial and/or transportation sounds, allergens, animal hair, pollen, exhaust from engines, vapors and/or fumes, fuel, signatures for mineral deposits and/or oil deposits, snow, rain, thermal energy, hot surfaces, hot gases, solar energy, hail, ice, vibrations, traffic, the number of people in a vicinity of the person, coughing and/or sneezing sounds from people in the vicinity of the person, loudness and/or pitch from those speaking in the vicinity of the person.

According to some embodiments of the present invention, earbuds for headsets may include a chipset having at least one sensor element, noise source element, signal processor, input/output line, digital control, and power regulator.

Light-guiding earbuds according to the various embodiments of the present invention may be utilized with mono headsets (i.e., headsets having one earbud) as well as stereo headsets (i.e., headsets having two earbuds). Additionally, the light-guiding region of earbuds, according to embodiments of the present invention, may be integrated not only into an earbud cover and earbud housing, but also into each or all components of an earbud. Moreover, light-guiding earbuds according to the various embodiments of the present invention may be utilized with hearing aids, body jewelry, or any other attachment that can be placed near the head region, such as eye glasses or shades, a headband, a cap, helmet, visor, or the like.

According to some embodiments of the present invention, a monitoring device includes a circular band capable of encircling a finger of a subject, and a base having an optical emitter and an optical detector attached to the circular band. The circular band includes light transmissive material in optical communication with the optical emitter and optical detector that is configured to deliver light from the optical emitter to one or more portions of the finger of the subject and to collect light from one or more portions of the finger of the subject and deliver the collected light to the optical detector. In some embodiments, the circular band includes first and second concentric body portions.

In some embodiments, the circular band includes a lens region in optical communication with the optical emitter that focuses light emitted by the optical emitter and/or that collects light reflected from a finger. In some embodiments the circular band includes a phosphor-containing region in optical communication with the light transmissive material, wherein the phosphor-containing region receives light emitted by the optical emitter and converts at least a portion of the received light to light having a different wavelength from the received light.

In some embodiments, the light transmissive material of the circular band has an outer surface and an inner surface, and a cladding material, such as light reflective material, is on (or near) at least a portion of one or both of the inner and outer surfaces.

In some embodiments, the base includes one or more of the following: a signal processor configured to receive and process signals produced by the optical detector, a transmitter configured to transmit signals processed by the signal processor to a remote device.

According to some embodiments of the present invention, a monitoring device configured to be attached to the body of a subject includes a base having an optical emitter and an optical detector, and light transmissive material attached to the base. The light transmissive material is in optical communication with the optical emitter and optical detector and is configured to deliver light from the optical emitter to one or more portions of the body of the subject and to collect light from one or more portions of the body of the subject and deliver the collected light to the optical detector. The light transmissive material may include adhesive material in one or more locations that is configured to adhesively secure the device to the body of the subject.

In some embodiments, an outer body portion is attached to the base and to the light transmissive material. The outer body portion may include adhesive material in one or more locations that is configured to adhesively secure the device to the body of the subject.

In some embodiments, the light transmissive material includes a lens region that is in optical communication with the optical emitter and that focuses light emitted by the optical emitter and/or that collects light reflected from a finger. In some embodiments, the light transmissive material includes a phosphor-containing region that receives light emitted by the optical emitter and converts at least a portion of the received light to light having a different wavelength from the received light. In some embodiments, the light transmissive material has an outer surface and an inner surface, and a light reflective material is disposed on or near at least a portion of one or both of the inner and outer surfaces.

In some embodiments, the base includes one or more of the following: a signal processor configured to receive and process signals produced by the optical detector, a transmitter configured to transmit signals processed by the signal processor to a remote device.

According to some embodiments of the present invention, a headset includes a housing that is configured to be positioned within an ear of a subject, an optical emitter, an optical detector, and at least one light guide associated with the housing. The headset may include a speaker disposed within the housing, and the housing may include at least one aperture through which sound from the speaker can pass. The headset may also include a signal processor that is configured to receive and process signals produced by the optical detector.

The at least one light guide includes a distal end that is configured to engage (or be positioned adjacent) a portion of the ear of the subject. An opposite end of the at least one light guide is in optical communication the optical emitter or optical detector. As such, the at least one light guide is configured to deliver light from the optical emitter into an ear region of the subject via the distal end or collect light from an ear region of the subject via the distal end or deliver collected light to the optical detector. In some embodiments, the optical emitter and optical detector may each have one or more respective light guides in optical communication therewith.

In some embodiments, the at least one light guide has a distal end portion that extends outwardly from the housing. In other embodiments, the at least one light guide has a distal end portion that is substantially flush with the housing or is recessed within the housing.

In some embodiments of the present invention, the optical emitter and optical detector are attached to the housing, such as the housing of the earbud itself. In other embodiments, the optical emitter and/or optical detector are located remotely from the housing. For example, the optical emitter and/or optical detector may be located on a headband, back-bar, back-band, ear hook, or any other structure that is a part of the headset. Moreover, the optical emitter and optical detector may be located at different respective locations anywhere on the headset. The at least one light guide extends from the remotely located optical emitter and/or optical detector and to the housing such that a distal end thereof can engage (or be positioned adjacent) a portion of the ear of the subject.

The at least one light guide may be formed from various types of light transmissive material, typically with a refractive index of at least one (1), and may have various shapes and configurations. For example, in some embodiments, the at least one light guide has an elongated, generally cylindrical configuration. In some embodiments, the at least one light guide comprises an elastomeric light transmissive material. In other embodiments, the at least one light guide comprises a substantially rigid light transmissive material. In some embodiments, the at least one light guide may be surrounded or partially surrounded by a cladding material that is configured to at least partially confine light within the light guide and/or block light from an external source from entering the at least one light guide. The cladding material may be a light blocking material and/or a light reflective material, such as a black or silver coating on one or more portions of the surface of the at least one light guide.

In some embodiments, a light blocking material is positioned between the optical emitter and detector such that the optical emitter and detector are not in direct optical communication with each other.

In some embodiments, optical coupling material is applied to the optical emitter and the at least one light guide is in optical communication with the optical emitter via the optical coupling material.

In some embodiments, optical coupling material is applied to the optical detector and the at least one light guide is in optical communication with the optical detector via the optical coupling material.

In some embodiments, a plurality of light guides are utilized, each having a distal end that engages a respective different portion of the ear of a subject.

In some embodiments, the headset includes a plurality of optical emitters and a plurality of light guides. The plurality of light guides are in optical communication with the plurality of optical emitters and are configured to deliver light from the plurality of optical emitters to an ear region of the subject.

In some embodiments, the headset includes a plurality of optical detectors and a plurality of light guides. The plurality of light guides are in optical communication with the plurality of optical detectors and configured to collect light from an ear region of the subject and deliver collected light to the plurality of optical detectors.

According to other embodiments of the present invention, a headset includes a housing configured to be positioned within an ear of a subject, an optical emitter, an optical detector, and first and second light guides associated with the housing. The headset may include a speaker disposed within the housing, and the housing may include at least one aperture through which sound from the speaker can pass. The headset may also include a signal processor that is configured to receive and process signals produced by the optical detector.

Each of the first and second light guides includes a distal end that is configured to engage (or be positioned adjacent) a respective portion of the ear of the subject. The first light guide is in optical communication with the optical emitter and is configured to deliver light from the optical emitter into an ear region of the subject via the first light guide distal end. The second light guide is in optical communication with the optical detector and is configured to collect light from an ear region of the subject via the second light guide distal end and deliver collected light to the optical detector.

In some embodiments, the distal end of the first and/or second light guides extends outwardly from the housing. In other embodiments, the distal end of the first and/or second light guides is substantially flush with the housing or is recessed within the housing.

In some embodiments of the present invention, the optical emitter and optical detector are attached to the housing. In other embodiments, the optical emitter and/or optical detector are located remotely from the housing. For example, the optical emitter and optical detector may be located on a headband or other structure that is a part of the headset. The first and second light guides extend from the remotely located optical emitter and optical detector and to the housing such that a distal end of each can engage (or be positioned adjacent) a respective portion of the ear of the subject.

The first and second light guides may be formed from various types of light transmissive material, typically with a refractive index of at least one (1), and may have various shapes and configurations. For example, in some embodiments, one or both of the first and second light guides have an elongated, generally cylindrical configuration. In some embodiments, one or both of the first and second light guides may comprise an elastomeric light transmissive material. In other embodiments, one or both of the first and second light guides may comprise a substantially rigid light transmissive material. Examples of suitable soft or elastomeric materials may include, but are not limited to, silicone, rubber, polymer-based materials, latex, lower durometer plastics, and the like. Examples of suitable rigid materials may include, but are not limited to, polyurethane, polymer-based materials, resins, higher durometer plastics, polycarbonate, acrylic, and the like.

In some embodiments, one or both of the first and second light guides may be surrounded or may be partially surrounded by a cladding material that is configured to block light from an external source and/or at least partially confine light within one or both of the first and second light guides. The cladding material may be a light blocking material and/or a light reflective material. In some embodiments, the cladding material may be a coating, such as a black, mylar, gold, or silver coating, or a textured surface, on one or more portions of the surface of the first and second light guides. In some embodiments, the cladding may be a texturized or specially treated surface of the light guide itself, such as a micro- or nano-structured surface or an electrochemically or chemically treated surface. Surface texturing can be used to scatter internal light back within the light guide or to scatter external light away from the light guide.

In some embodiments, the light guide may also be and/or comprise an optical filter. This may provide a structure that provides both light guiding of the desired wavelengths and light blocking of undesired wavelengths. For example, the light-guide may comprise a material having an optically filtering dye or a material which inherently filters one or more wavelengths of light. For example, a light-absorptive dye, many of which are well-known in the art, may be integrated within or coated on top a polycarbonate or acrylic sheet. Similarly, a light-absorptive dye may be integrated within a resin which may then be molded into one or more light guides. A few non-limiting examples of an inherently filtering material includes sapphire, which absorbs some infrared (IR) wavelengths, or glass, which absorbs some ultraviolet (UV) wavelengths. However, various types of filtering material may be utilized, without limitation.

According to other embodiments of the present invention, a headset includes a housing configured to be positioned within an ear of a subject, an optical emitter, an optical detector, and a light guide associated with the housing. The headset may include a speaker disposed within the housing, and the housing may include at least one aperture through which sound from the speaker can pass. The headset may also include
a signal processor that is configured to receive and process signals produced by the optical detector.

The light guide includes a distal end that is configured to engage (or be positioned adjacent) a portion of the ear of the subject. An opposite end of the light guide is in optical communication with the optical emitter and the optical detector. As such, the light guide is configured to deliver light from the optical emitter into an ear region of the subject via the light guide distal end, and to collect light from the ear region of the subject via the light guide distal end and deliver collected light to the optical detector.

In some embodiments, the light guide has a distal end portion that extends outwardly from the housing. In other embodiments, the light guide has a distal end portion that is substantially flush with the housing or is recessed within the housing.

In some embodiments of the present invention, the optical emitter and optical detector are attached to the housing. In other embodiments, the optical emitter and/or optical detector are located remotely from the housing. For example, the optical emitter and/or optical detector may be located on a headband or any other structure that is a part of the headset. Moreover, the optical emitter and optical detector may be located at different respective locations anywhere on the headset. The light guide extends from the remotely located optical emitter and optical detector and to the housing such that a distal end thereof can engage (or be positioned adjacent) a portion of the ear of the subject.

The light guide may be formed from various types of light transmissive material, typically with a refractive index of at least one (1), and may have various shapes and configurations. For example, in some embodiments, the light guide has an elongated, generally cylindrical configuration. In some embodiments, the light guide comprises an elastomeric light transmissive material. In other embodiments, the light guide comprises a substantially rigid light transmissive material. In some embodiments, the light guide may be surrounded or partially surrounded by a cladding material that is configured to block light from an external source from entering the at least one light guide and/or at least partially confine light within the light guide. The cladding material may be a light blocking material and/or a light reflective material, such as a black or silver coating on one or more portions of the surface of the light guide.

According to other embodiments of the present invention, a wearable sensor module includes a housing configured to be worn by a subject, an optical emitter, an optical detector, and at least one light guide extending outwardly from the housing. The at least one light guide includes a distal end that is configured to engage (or be positioned adjacent) a skin region of the subject. An opposite end of the at least one light guide is in optical communication with the optical emitter or optical detector. As such, the at least one light guide is configured to deliver light from the optical emitter into a skin region the subject via the distal end or collect light from a skin region of the subject via the distal end and deliver collected light to the optical detector. In some embodiments, the optical emitter and optical detector may each have one or more respective light guides in optical communication therewith.

In some embodiments of the present invention, the optical emitter and optical detector are attached to the housing. In other embodiments, the optical emitter and/or optical detector are located remotely from the housing.

The at least one light guide may be formed from various types of light transmissive material, typically with a refractive index of at least one (1), and may have various shapes and configurations. For example, in some embodiments, the at least one light guide has an elongated, generally cylindrical configuration. In some embodiments, the at least one light guide comprises an elastomeric light transmissive material. In other embodiments, the at least one light guide comprises a substantially rigid light transmissive material. In some embodiments, the at least one light guide may be surrounded or partially surrounded by a cladding material that is configured to block light from an external source from entering the at least one light guide and/or at least partially confine light within the at least one light guide.

In some embodiments, light blocking material is positioned between the optical emitter and detector such that the optical emitter and detector are not in direct optical communication with each other.

In some embodiments, optical coupling material is applied to the optical emitter and the at least one light guide is in optical communication with the optical emitter via the optical coupling material.

In some embodiments, optical coupling material is applied to the optical detector and the at least one light guide is in optical communication with the optical detector via the optical coupling material.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate various embodiments of the present invention. The drawings and description together serve to fully explain embodiments of the present invention.

FIG. 7A is a side section view of a light-guiding earbud for a headset, according to some embodiments of the present invention.

FIG. 7B is a perspective view of a flexible optical emitter utilized in the earbud of FIG. 7A, according to some embodiments of the present invention.

FIG. 8A is a side section view of a light-guiding earbud for a headset, according to some embodiments of the present invention.

FIG. 8B is a cross-sectional view of the earbud of FIG. 8A taken along lines 8B-8B.

FIG. 11A is a side section view of a light-guiding earbud for a headset, according to some embodiments of the present invention.

FIG. 11B is a cross-sectional view of the earbud of FIG. 11A taken along lines 11B-11B.

FIGS. 12A-12B illustrate respective opposite sides of a sensor module that may be located near the periphery of an earbud, according to some embodiments of the present invention.

FIG. 23 is a side view of a monitoring device configured to be attached to the body of a subject, according to some embodiments of the present invention.

DETAILED DESCRIPTION

Figure 1:
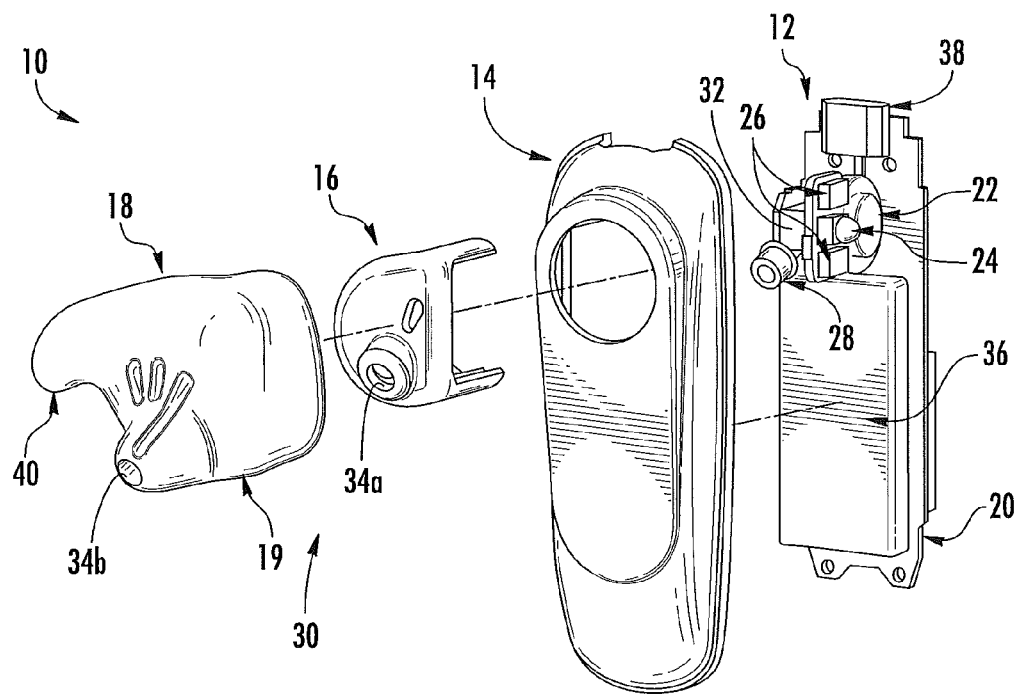
FIG. 1 is an exploded perspective view of a headset with a light-guiding earbud, according to some embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various features/elements, these features/elements should not be limited by these terms. These terms are only used to distinguish one feature/element from another feature/element. Thus, a first feature/element discussed below could be termed a second feature/element, and similarly, a second feature/element discussed below could be termed a first feature/element without departing from the teachings of the present invention. Like numbers refer to like elements throughout.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "headset", as used herein, is intended to include any type of device or earpiece that may be attached to or near the ear (or ears) of a user and may have various configurations, without limitation. Headsets incorporating light-guiding earbuds, as well as light guides, as described herein may include mono headsets (a device having only one earbud, one earpiece, etc.) and stereo headsets (a device having two earbuds, two earpieces, etc.), earbuds, hearing aids, ear jewelry, face masks, headbands, and the like. In some embodiments, the term "headset" may include broadly headset elements that are not located on the head but are associated with the headset. For example, in a "medallion" style wireless headset, where the medallion comprises the wireless electronics and the headphones are plugged into or hard-wired into the medallion, the wearable medallion would be considered part of the headset as a whole. Similarly, in some cases, if a mobile phone or other mobile device is intimately associated with a plugged-in headphone, then the term "headset" may refer to the headphone-mobile device combination.

The term "real-time" is used to describe a process of sensing, processing, or transmitting information in a time frame which is equal to or shorter than the minimum timescale at which the information is needed. For example, the real-time monitoring of pulse rate may result in a single average pulse-rate measurement every minute, averaged over 30 seconds, because an instantaneous pulse rate is often useless to the end user. Typically, averaged physiological and environmental information is more relevant than instantaneous changes. Thus, in the context of the present invention, signals may sometimes be processed over several seconds, or even minutes, in order to generate a "real-time" response.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "physiological" refers to matter or energy of or from the body of a creature (e.g., humans, animals, etc.). In embodiments of the present invention, the term "physiological" is intended to be used broadly, covering both physical and psychological matter and energy of or from the body of a creature. However, in some cases, the term "psychological" is called-out separately to emphasize aspects of physiology that are more closely tied to conscious or subconscious brain activity rather than the activity of other organs, tissues, or cells.

The term "body" refers to the body of a subject (human or animal) that may wear a headset incorporating one or more light-guiding earbuds, according to embodiments of the present invention.

In the following figures, various headsets and light-guiding earbuds for use with headsets will be illustrated and described for attachment to the ear of the human body. However, it is to be understood that embodiments of the present invention are not limited to those worn by humans.

The ear is an ideal location for wearable health and environmental monitors. The ear is a relatively immobile platform that does not obstruct a person's movement or vision. Headsets located at an ear have, for example, access to the inner-ear canal and tympanic membrane (for measuring core body temperature), muscle tissue (for monitoring muscle tension), the pinna and earlobe (for monitoring blood gas levels), the region behind the ear (for measuring skin temperature and galvanic skin response), and the internal carotid artery (for measuring cardiopulmonary functioning), etc. The ear is also at or near the point of exposure to: environmental breathable toxicants of interest (volatile organic compounds, pollution, etc.; noise pollution experienced by the ear; and lighting conditions for the eye. Furthermore, as the ear canal is naturally designed for transmitting acoustical energy, the ear provides a good location for monitoring internal sounds, such as heartbeat, breathing rate, and mouth motion.

Wireless, Bluetooth®-enabled, and/or other personal communication headsets may be configured to incorporate physiological and/or environmental sensors, according to some embodiments of the present invention. As a specific example, Bluetooth® headsets are typically lightweight, unobtrusive devices that have become widely accepted socially. Moreover, Bluetooth® headsets are cost effective, easy to use, and are often worn by users for most of their waking hours while attending or waiting for cell phone calls. Bluetooth® headsets configured according to embodiments of the present invention are advantageous because they provide a function for the user beyond health monitoring, such as personal communication and multimedia applications, thereby encouraging user compliance. Exemplary physiological and environmental sensors that may be incorporated into a Bluetooth® or other type of headsets include, but are not limited to accelerometers, auscultatory sensors, pressure sensors, humidity sensors, color sensors, light intensity sensors, pressure sensors, etc.

Headsets, both mono (single earbud) and stereo (dual earbuds), incorporating low-profile sensors and other electronics, according to embodiments of the present invention, offer a platform for performing near-real-time personal health and environmental monitoring in wearable, socially acceptable devices. The capability to unobtrusively monitor an individual's physiology and/or environment, combined with improved user compliance, is expected to have significant impact on future planned health and environmental exposure studies. This is especially true for those that seek to link environmental stressors with personal stress level indicators. The large scale commercial availability of this low-cost device can enable cost-effective large scale studies. The combination of monitored data with user location via GPS data can make on-going geographic studies possible, including the tracking of infection over large geographic areas. The commercial application of the proposed platform encourages individual-driven health maintenance and promotes a healthier lifestyle through proper caloric intake and exercise.

Accordingly, some embodiments of the present invention combine a personal communications headset device with one or more physiological and/or environmental sensors. Other embodiments may combine physiological and/or environmental sensors into a headset device.

Optical coupling into the blood vessels of the ear may vary between individuals. As used herein, the term "coupling" refers to the interaction or communication between excitation light entering a region and the region itself. For example, one form of optical coupling may be the interaction between excitation light generated from within a light-guiding earbud and the blood vessels of the ear. In one embodiment, this interaction may involve excitation light entering the ear region and scattering from a blood vessel in the ear such that the intensity of scattered light is proportional to blood flow within the blood vessel. Another form of optical coupling may be the interaction between excitation light generated by an optical emitter within an earbud and the light-guiding region of the earbud. Thus, an earbud with integrated light-guiding capabilities, wherein light can be guided to multiple and/or select regions along the earbud, can assure that each individual wearing the earbud will generate an optical signal related to blood flow through the blood vessels. Optical coupling of light to a particular ear region of one person may not yield photoplethysmographic signals for each person. Therefore, coupling light to multiple regions may assure that at least one blood-vessel-rich region will be interrogated for each person wearing the light-guiding earbud. Coupling multiple regions of the ear to light may also be accomplished by diffusing light from a light source within the earbud.

Embodiments of the present invention are not limited to headsets that communicate wirelessly. In some embodiments of the present invention, headsets configured to monitor an individual's physiology and/or environment may be wired to a device that stores and/or processes data. In some embodiments, this information may be stored on the headset itself. Furthermore, embodiments of the present invention are not limited to earbuds. In some embodiments, the light-guiding structure may be molded around another part of the body, such as a digit, finger, toe, limb, around the nose or earlobe, or the like. In other embodiments, the light-guiding structure may be integrated into a patch, such as a bandage that sticks on a person's body.

Referring to FIG. 1, a headset 10 according to some embodiments of the present invention is illustrated. The illustrated headset 10 includes a base 12, a headset housing 14, an earbud housing 16, and a cover 18 that surrounds the earbud housing 16. The base 12 includes a main circuit board 20 that supports and/or is connected to various electronic components. In the illustrated embodiment, a speaker 22, optical emitter 24, optical detectors 26, and thermopile 28 (described below) are mounted onto a secondary circuit board 32 which is secured to the main circuit board 20. The earbud housing surrounds the speaker 22, optical emitter 24, optical detectors 26, and thermopile 28. Collectively, the earbud housing 16, cover 18, and various electronic components (e.g., speaker 22, optical emitter 24, optical detectors 26, thermopile 28) located within the earbud housing 16 of the illustrated headset 10 may be referred to as an earbud 30. The headset housing 14 is secured to the base 12 and is configured to enclose and protect the various electronic components mounted to the base (e.g., main circuit board 20 and components secured thereto, etc.) from ambient interference (air, humidity, particulates, electromagnetic interference, etc).

Each optical detector 26 may be a photodiode, photodetector, phototransistor, thyristor, solid state device, optical chipset, or the like. The optical emitter 24 may be a light-emitting diode (LED), laser diode (LD), compact incandescent bulb, micro-plasma emitter, IR blackbody source, or the like. The speaker 22 may be a compact speaker, such as an inductive speaker, piezoelectric speaker, electrostatic speaker, or the like. One or more microphones, such as electrets, MEMS, acoustic transducers, or the like, may also be located within the headset housing or earbud housing to pick up speech, physiological sounds, and/or environmental sounds.

The main circuit board 20 and secondary circuit board 32 may also support one or more sensor modules (not shown) that contain various physiological and/or environmental sensors. For example, a sensor module, such as sensor module 70 illustrated in FIGS. 12A-12B, may be attached to the circuit boards 20, 32. The circuit boards 20, 32 also may include at least one signal processor (not shown), at least one wireless module (not shown) for communicating with a remote device, and/or at least one memory storage device (not shown). An exemplary wireless module may include a wireless chip, antenna, or RFID tag. In some embodiments, the wireless module may include a low-range wireless chip or chipset, such as a Bluetooth® or ZigBee chip. These electronic components may be located on the main circuit board 20, or on another circuit board, such as the secondary circuit board 32, attached to the main circuit board.

Secondary circuit board 32 may also include a temperature sensor, such as a thermopile 28 mounted thereto. The thermopile 28 is oriented so as to point towards the tympanic membrane within the ear of a subject wearing the headset 10 through the acoustic orifices 34a, 34b in the earbud housing 16 and cover 18, respectively. The secondary circuit board 32 may be in electrical contact with the main circuit board 20 via soldering, connectors, wiring, or the like. A battery 36, such as a lithium polymer battery or other portable battery, may be mounted to the main circuit board 20 and may be charged via a USB charge port 38. Although not shown in FIG. 1, an ear hook may be attached to the base 12 or housing 14 to help stabilize the earbud 30 and headset 10 worn by a subject and such that the earbud 30 is consistently placed at the same location within the ear canal of a subject.

In the illustrated embodiment, the earbud housing 16 is in acoustical communication with the speaker 22 and includes an aperture 34a through which sound from the speaker 22 can pass. However, additional apertures may also be utilized. The cover 18 also includes at least one aperture 34b through which sound from the speaker 22 can pass. The thermopile 28 is used as a heat sensor and measures thermal radiation from the ear of a subject via the acoustic apertures 34a, 34b. Additional or other sensors may be in the location of the thermopile 28, aligned towards the tympanic membrane, to sense other forms of energy, such as acoustic, mechanical, chemical, optical, or nuclear energy from the tympanic membrane region. For example, a photodetector may replace the thermopile 28 to measure light scattering off the tympanic membrane.

The cover 18 includes light transmissive material in a portion 19 thereof that is referred to as a light-guiding region. The light transmissive material in light-guiding region 19 is in optical communication with the optical emitter 24 and detectors 26. The light transmissive material in light-guiding region 19 is configured to deliver light from the optical emitter 24 into an ear canal of the subject at one or more predetermined locations and to collect light external to the earbud 30 and deliver the collected light to the optical detectors 26. As such, the earbud 30 of the illustrated headset 10 is referred to as a "light-guiding" earbud 30.

Figure 5:
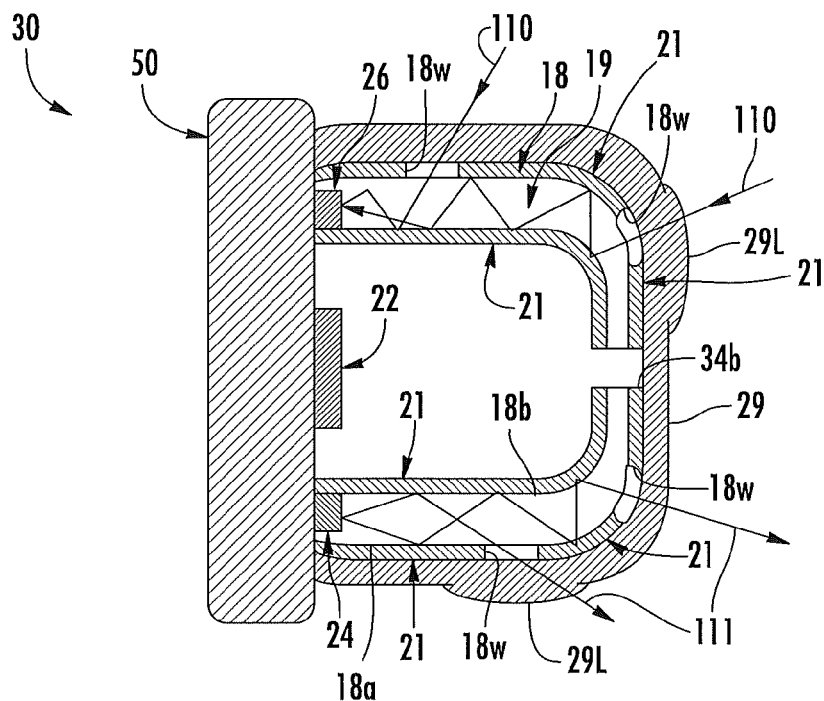
FIG. 5 is a side section view of a light-guiding earbud for a headset, according to some embodiments of the present invention.
Figure 6:
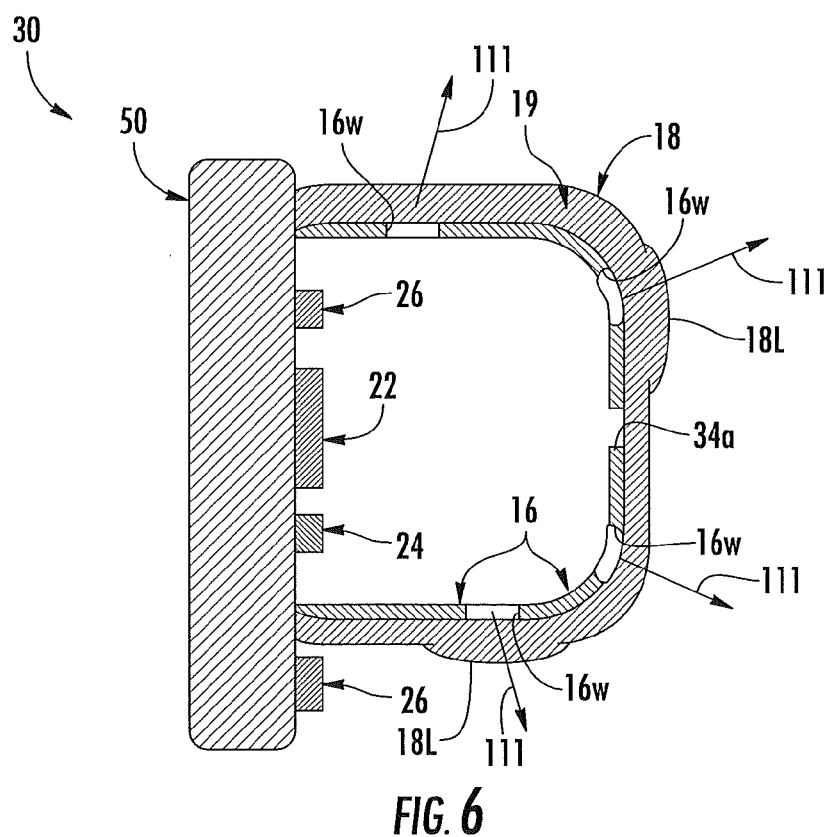
FIG. 6 is a side section view of a light-guiding earbud for a headset, according to some embodiments of the present invention.

In some embodiments, the light transmissive material in the light-guiding region 19 may include a lens (e.g., lens 18L illustrated in FIG. 6). The lens 18L is in optical communication with the optical emitter 24 and/or with the optical detectors 26. For example, a lens 18L may be configured to focus light emitted by the optical emitter 24 onto one or more portions of an ear and/or to focus collected light on the light detectors 26. Lenses are described below with respect to FIGS. 5-6.

In some embodiments, the earbud cover 18 may integrate a transparent light-guiding layer, wherein air is utilized as a cladding layer. For example, the earbud cover 18 may include an optically transparent silicone molded layer, and the earbud housing 16 may be removed such that a cladding layer is air. In some embodiments, the earbud housing 16 may be closed, and the light-guiding region 19 may be integrated within the cover 18 or between the housing 16 and cover 18.

The illustrated cover 18 of FIG. 1 includes an alignment member 40 (also referred to as a stabilization arm) that facilitates alignment of the earbud 30 within an ear canal of a subject. The alignment member 40 may facilitate stable measurements of optical scattered light from the ear region, which can be important for PPG measurements and tympanic temperature measurements.

In some embodiments, a light-guiding cover 18 is formed from a soft, resilient material, such as silicone, which deforms when inserted within an ear canal of a subject. However, various materials may be utilized for light-guiding covers 18 and for serving as light guides depending on the type of earbud desired for a particular use case, according to embodiments of the present invention. For example, in some embodiments, a light-guiding cover 18 may be formed from a substantially rigid material such that the light-guiding earbud 30 is substantially rigid. For example, for a running use case, the runner may wish to have firm but soft earbuds, such that the earbud may deform to some extent when inserted into the ear. In such case, the light-guiding region may be silicone or other soft material and the outer cladding may be air, a polymer, plastic, or a soft material having a lower index of refraction than silicone.

Figure 2:
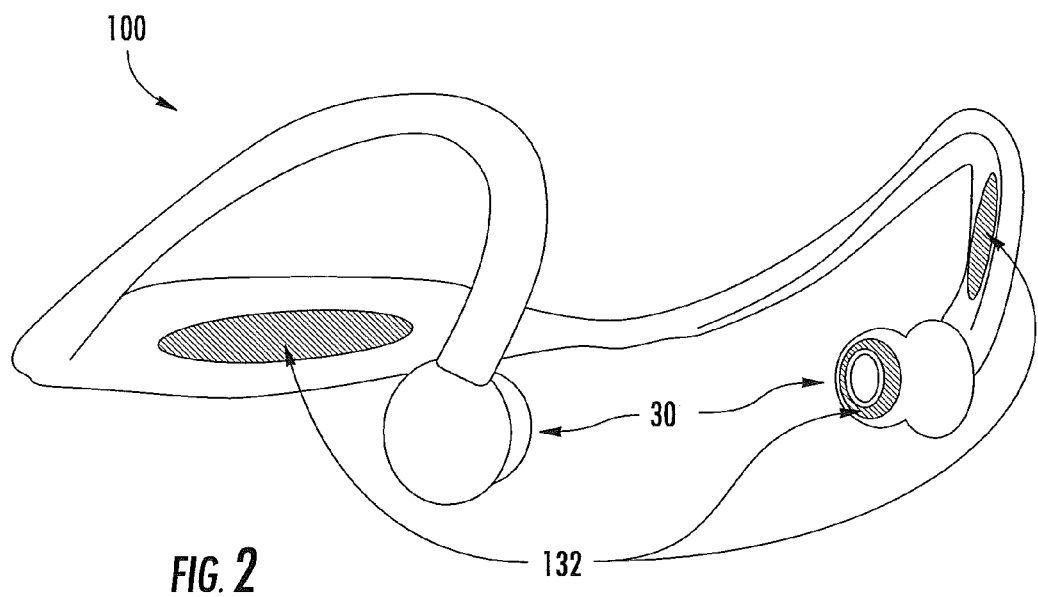
FIG. 2 is a perspective view of a stereo headset incorporating light-guiding earbuds, according to some embodiments of the present invention.

FIG. 2 illustrates a stereo headset 100 that utilizes two light-guiding earbuds 130, according to some embodiments of the present invention. The headset 100 also includes various sensor elements 132 located at several regions in the stereo headset 100. A benefit of the stereo headset 100 may be that the total number of sensors measuring the ear region may be doubled; alternatively, the sensors in each earbud may be halved. Another benefit of the stereo headset is that it may enable stereo music during daily activities. Another benefit of the stereo headset is that asymmetric physiological differences can be detected in the user by measuring each side of the user in real-time. For example, differences in blood flow between right and left sides of a user may be detected, indicating changes in right/left brain activity, the onset of a stroke, localized inflammation, or the like.

Figure 3:
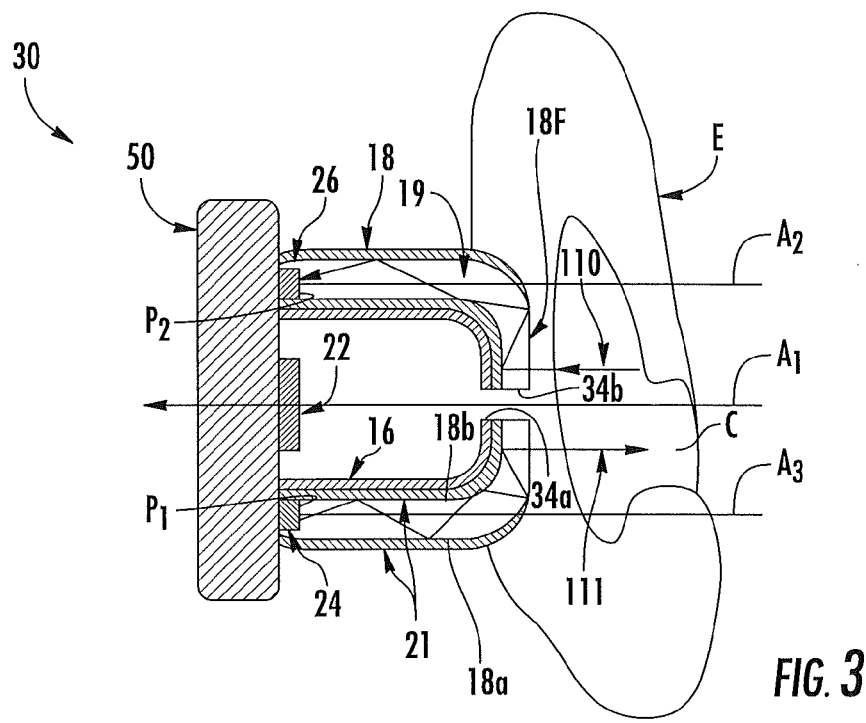
FIG. 3 is a side section view of a light-guiding earbud for a headset, according to some embodiments of the present invention.

Light-guiding earbuds according to various embodiments of the present invention will now be described with respect to FIGS. 3, 4A-4D, 5, 6, 7A-7B, 8A-8D, 9A-9B, and 11A-11B. Referring initially to FIGS. 3-4, a light-guiding earbud 30 includes a base 50, an earbud housing 16 extending outwardly from the base 50 that is configured to be positioned within an ear E of a subject, and a cover 18 that surrounds the earbud housing 16. The earbud housing 16 is in acoustical communication with a speaker 22 and includes at least one aperture 34a through which sound from the speaker 22 can pass. The cover 18 includes at least one aperture 34b through which sound from the speaker 22 can pass, and includes light transmissive material in optical communication with an optical emitter 24 and detector 26.

The cover 18 includes cladding material 21 on an inner surface 18b thereof and on an outer surface 18a thereof, as illustrated. An end portion 18f of the cover outer surface 18a does not have cladding material. As such, the cover 18 serves as a light guide that delivers light from the optical emitter 24 through the end portion 18f and into the ear canal C of a subject at one or more predetermined locations and that collects light external to the earbud housing 16 and delivers the collected light to the optical detector 26. In the various embodiments described herein, the terms light guide and cover are intended to be interchangeable. However, it should be noted that, in other embodiments, the earbud housing 16 may also serve as a light guide without the need for cover 18.

The base 50 in all of the earbud embodiments (FIGS. 3, 4A-4D, 5, 6, 7A-7B, 8A-8D, 9A-9B, 11A-11B, 24A-24B, 25A-25B, 26-29, 31, and 34) described herein may include any combination of a printed circuit board, electrical connectors, and housing component for a headset. For example, the base 50 in FIGS. 3-6, 7A-7B, 8A-8D, 9A-9B, 11A-11B, 24A-24B, 25A-25B, 26-29, 31, and 34 may include, for example, the base 12 of the headset 10 of FIG. 1, the main circuit board 20 of the headset 10 of FIG. 1, the housing 14 of the headset 10 of FIG. 1, or may be a combination of the base 12, main circuit board 20, and/or housing 14 of the headset 10 of FIG. 1.

The optical emitter 24 generates inspection light 111 and the light-guiding region 19 of the light guide 18 directs the inspection light 111 towards an ear region. This light is called inspection light because it interrogates the surface of the ear, penetrates the skin of the ear, and generates a scattered light response 110 which may effectively inspect blood vessels within the ear region. The optical detector 26 detects scattered light 110 from an ear region and the light-guiding region 19 of the light guide 18 guides the light to the optical detector 26 through the light-guiding region 19, as illustrated.

In the embodiment of FIG. 3, the light-guiding earbud 30 is configured for optical coupling that is parallel to the light guide (i.e., cover 18). The optical detector 26 and optical emitter 24 are configured to detect and generate light substantially parallel to the light-guiding region 19 of the light guide 18. For example, the light guide 18 defines an axial direction $A_1$. The optical emitter 24 and optical detector 26 are each oriented such that their respective primary emitting and detecting planes $P_1$, $P_2$ are each facing a respective direction $A_3$, $A_2$ that is substantially parallel with direction $A_1$.

The light guiding region 19 of the light guide 18 in the illustrated embodiment of FIG. 3 is defined by cladding material 21 that helps confine light within the light guiding region 19. The cladding material 21 may be reflective material in some embodiments. In other embodiments, the cladding material may be optically transparent or mostly transparent with a lower index of refraction than the light transmissive material of the cover 18. The cladding 21 may be a layer of material applied to one or more portions of the inner and/or outer surfaces 18a, 18b of the light guide 18. In some embodiments, the outer surface 16a of the earbud housing 16 may serve as cladding that confines light within the light-guiding region 19. In some embodiments, the light transmissive material of the light guide 18 may be composed of a material having a higher index of refraction than the cladding material 21. In some embodiments, air may serve as a cladding layer.

Figure 4A:
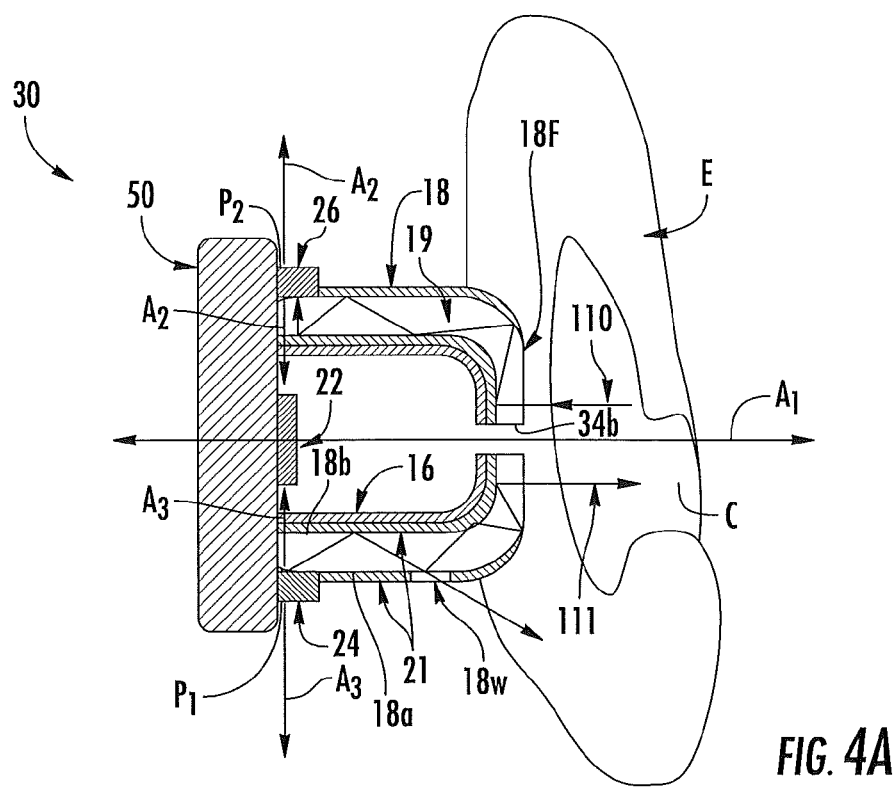
FIGS. 4A-4D are side section views of light-guiding earbuds for a headset, according to some embodiments of the present invention.

In the embodiment of FIG. 4A, the light-guiding earbud 30 is configured for optical coupling that is substantially perpendicular to the light guide (i.e., cover 18). The optical detector 26 and optical emitter 24 are configured to detect and generate light substantially perpendicular to the light-guiding region 19 of the light guide 18. For example, the light guide 18 defines an axial direction $A_1$. The optical emitter 24 and optical detector 26 are each oriented such that their respective primary emitting and detecting planes $P_1$, $P_2$ are each facing a respective direction $A_3$, $A_2$ that is substantially perpendicular to direction $A_1$. The orientation of the optical emitter 24 and optical detector 26 in FIG. 4A may be convenient for manufacturing purposes, where side-emitting LEDs and side-detecting photodetectors can couple directly to the light-guiding region 19 for generating light 111 and detecting light 110. This may relax size constraints for an earbud 30 because the dimensions of the light-guiding region 19 may be independent of the optical emitter 24 and optical detector 26.

Figure 4B:
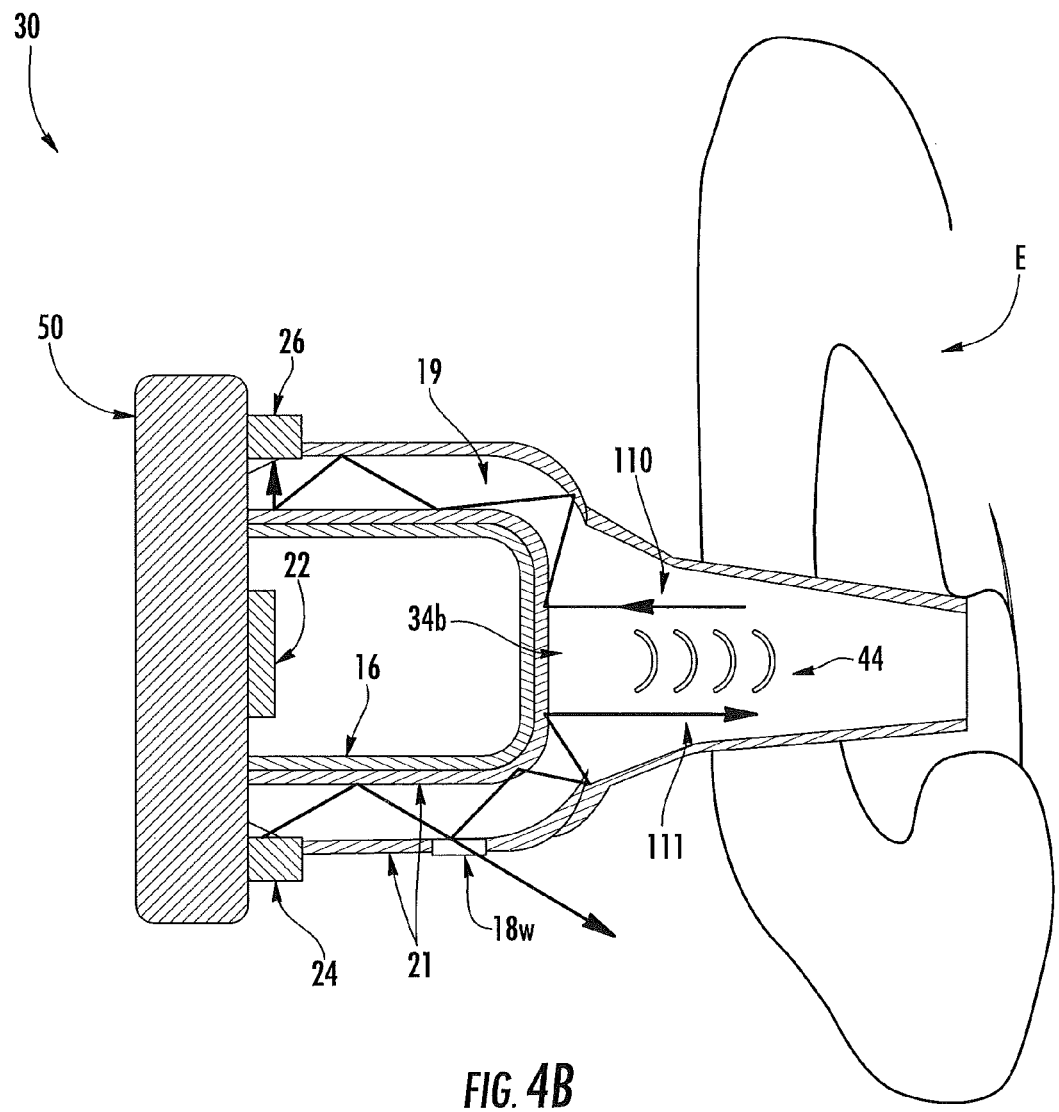

FIG. 4B illustrates the light-guiding earbud 30 of FIG. 4A modified such that the earbud cover 18 and cladding material 21 are elongated to reach deeper within the ear canal C of a subject, and closer to the tympanic membrane, for example. In the illustrated embodiment of FIG. 4B, there are no apertures in the housing 16 or cover 18. Acoustic energy 44 from/to the speaker/microphone passes through the material of the cover 18 and housing 16. The illustrated elongated configuration serves as both an optical light-guiding region and an acoustic wave-guiding region.

Figure 4C:
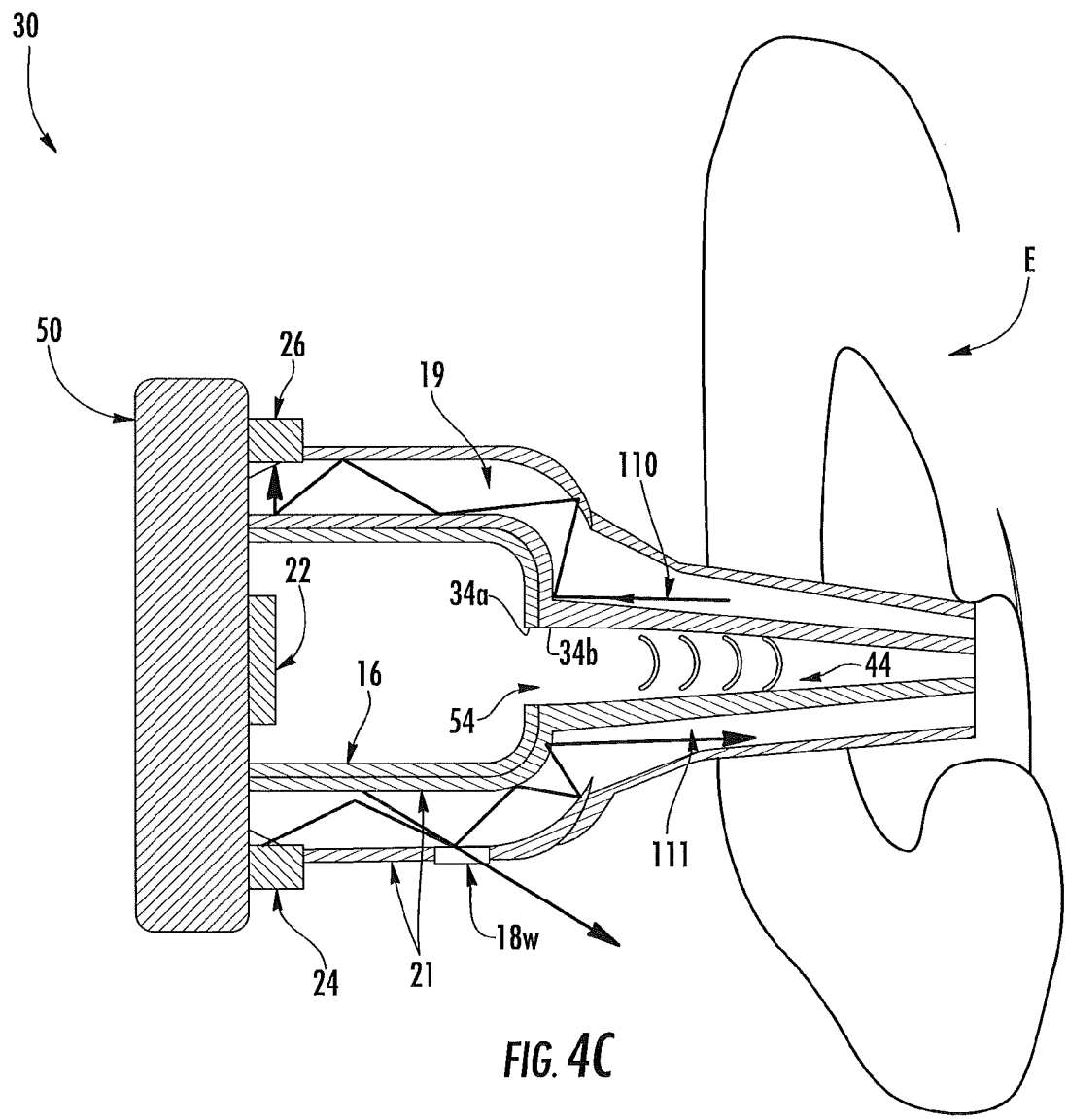

FIG. 4C illustrates the light-guiding earbud 30 of FIG. 4A modified such that the earbud cover 18 and cladding material 21 are elongated to reach deeper within the ear canal C of a subject, and closer to the tympanic membrane, for example. In the illustrated embodiment of FIG. 4C, apertures 34a, 34b in the housing 16 and cover 18 are provided. As such, the optical light-guiding region 19 and the acoustic wave-guiding region 54 are isolated from each other. The light-guiding region 19 may be a light transmissive material, such as a dielectric material, and the acoustic wave-guiding region 54 may be air or another material, and the separation between these regions may be defined by at least part of the cladding material 21. Embodiments of the present invention may include multiple openings 34a, 34b in the housing 16 and cover 18. The separation between the light-guiding region 19 and the acoustic wave-guiding region 54 may be defined by other structures composed of a variety of possible materials. Specific examples of these materials include plastic molding, metals, polymeric structures, composite structures, or the like.

Figure 4D:
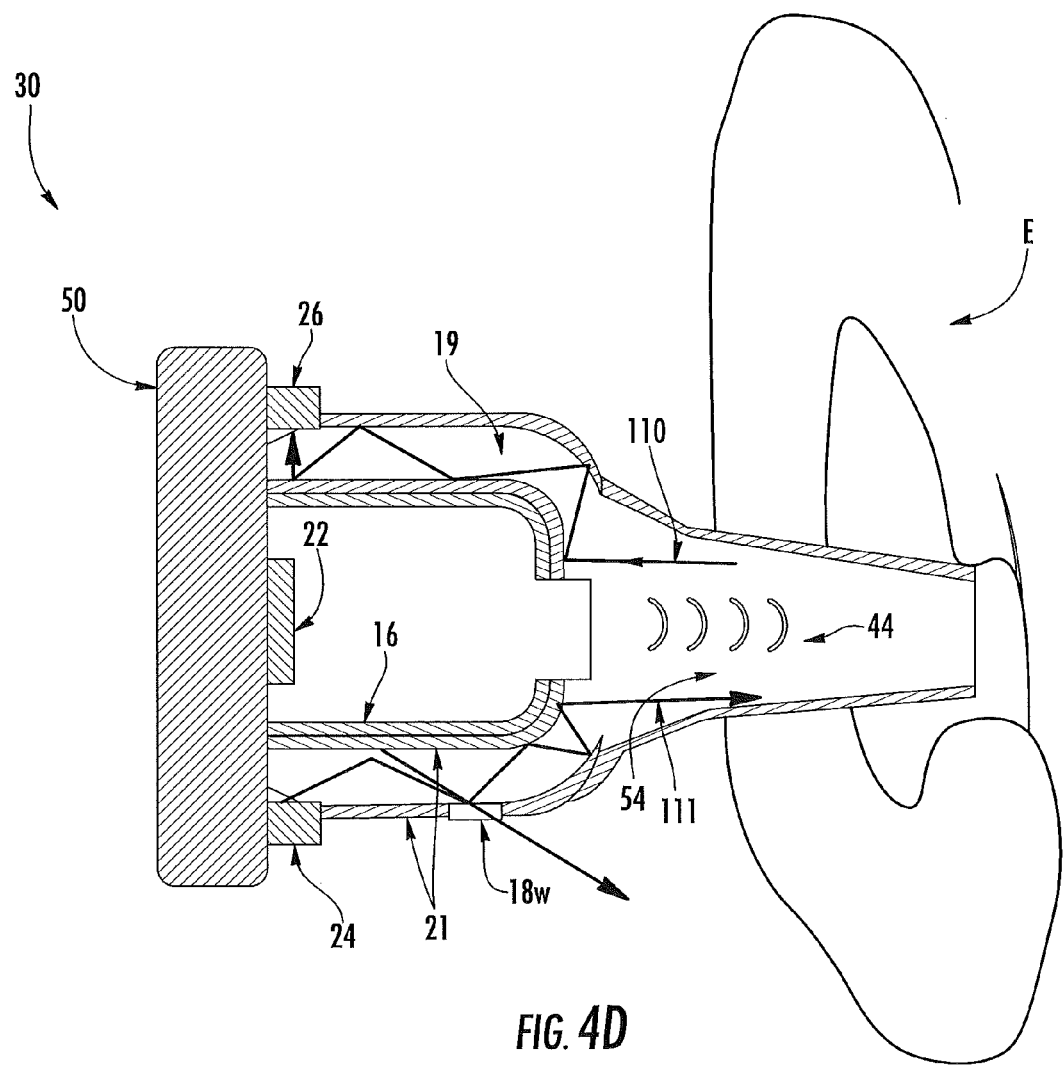

FIG. 4D illustrates the light-guiding earbud 30 of FIG. 4A modified such that the earbud cover 18 and cladding material 21 are elongated to reach deeper within the ear canal C of a subject, and closer to the tympanic membrane, for example. In the illustrated embodiment of FIG. 4D, the area within the housing 16 may be air, silicone, plastic, or any material capable of passing sound. As such, at opening 34b, an interface exists between the material of the light-guiding region 19 and the material within the housing 16. In some embodiments, the light-guiding region 19 and the region within the housing 16 may both be air. In other embodiments, the light-guiding region 19 and the region within the housing 16 may be formed from the same or different materials. In some embodiments, the region within the housing 16 may be formed from an optical wave guiding material identical or similar to the material in the light-guiding region 19.

In the embodiments of FIGS. 4B-4D, the optical energy 110 coming from the ear may include optical wavelengths, such as IR wavelengths, emitting from the tympanic membrane due to black body radiation. If the optical detector 26 is configured to measure this black body radiation, then the earbud can be used to measure tympanic temperature, blood analyte levels, neurological, electrical activity, or metabolic activity of the earbud wearer.

Referring to FIG. 5, a light-guiding earbud 30 is configured for optical coupling that is parallel to the light guide (i.e., cover 18) as in the embodiment of FIG. 3. However, the embodiment of FIG. 5 does not include a separate earbud housing. Instead, the light guide 18 serves the function of the earbud housing. In addition, the light guide 18 includes multiple windows 18w formed in the cladding material 21 on the outer surface 18a of the cover and through which light 111 emitted by the light emitter 24 passes and multiple windows 18w through which scattered light 110 passes into the light guide 18 to be directed to the light detector 26. These openings 18w may extend circumferentially around the light guide 18 or may partially extend circumferentially around portions of the light guide 18. In some embodiments of this invention, the earbud housing and light guide 18 may be separated, as shown in other figures.

In addition, the illustrated light guide 18 of FIG. 5 is surrounded by a layer 29 of light transmissive material. One or more lenses 29L are formed in this layer 29 and are in optical communication with respective windows 18w in the light guide 18. In the illustrated embodiment, a lens 29L is in optical communication with a respective window 18w through which emitted light 111 passes, and a respective window 18w through which scattered light 110 passes. Lenses 29L are configured to focus inspection light 111 onto a particular region of the ear. Lenses 29L are configured to help collect scattered light 110 and direct the scattered light 110 into the light guiding region 19. In some embodiments, these lenses 29L may be a molded part of the light guide 18. The illustrated location of lenses 29L in FIG. 5 is non-limiting, and the lenses 29L may be located wherever optical coupling between the earbud and ear is desired. Though convex lens embodiments are shown in FIG. 5, this is not meant to limit embodiments of the present invention. Depending on the desired optical coupling and configuration of the earbud against the ear, a variety of lens types and shapes may be useful, such as convex, positive or negative meniscus, planoconvex, planoconcave, biconvex, biconcave, converging, diverging, and the like.

Referring now to FIG. 6, a light guiding earbud 30, according to some embodiments of the present invention, includes a base 50, an earbud housing 16 extending outwardly from the base 50 that is configured to be positioned within an ear E of a subject, and a cover 18 of light transmissive material surrounding the earbud housing 16 that forms a light-guiding region 19. The earbud housing 16 is in acoustical communication with a speaker 22 and includes at least one aperture 34a through which sound from the speaker 22 can pass. The earbud housing 16 encloses the speaker 22, an optical emitter 24 and an optical detector 26 as illustrated. An additional light detector 26 is located on the base 50 but is not surrounded by the earbud housing 16.

The earbud housing 16 is formed of a cladding material. The cladding material may be reflective material in some embodiments. In other embodiments, the cladding material may be optically transparent or mostly transparent with a lower index of refraction than the light transmissive material of the cover 18. In some embodiments, the earbud housing 16 may be replaced by air, such that the cladding region is air. Air may have a smaller index of refraction than that of the cover 18, supporting light transmission along the cover 18. In other embodiments, a cladding region exists between the earbud housing 16 and the light-guiding region 19. In another embodiment, a cladding region exists covering the outside of light-guiding region 19, with the exception of regions surrounding the lens regions 18L.

A plurality of windows 16w are formed in the earbud housing 16 at selected locations to permit light emitted by the light emitter 24 to pass therethrough. In some embodiments, the earbud housing 16 may have translucent or transparent material that serves the function of one or more windows 16w. The cover 18 includes a plurality of lenses 18L that are in optical communication with respective windows 16w in the earbud housing 16. These lenses 18L are configured to focus light 111 passing through a respective window 16w towards a particular region of the ear of a subject, and to help collect scattered light 110 and direct the scattered light 110 into the earbud housing 16 towards the light detector 26.

The earbud 30 of FIG. 6, via the locations of windows 16w, produces isotropic optical coupling, such that the light generated by the optical emitter 24 is roughly identical in all directions with respect to the earbud housing 16. The inspection light 111 generated by the optical emitter 24 passes isotropically into the light guiding region 19 through the windows 16w.

A benefit of light guiding earbud 30 of FIG. 6 is that manufacturing may not require alignment of the light-guiding region 19 with respect to the optical emitter 24 and detector 26. This may be in part because the optical energy density generated/detected by the optical emitter/detector may be the same, or relatively uniform, within the earbud housing 16 regardless of alignment of the light guide 18 with respect to the earbud housing 16 or regardless of alignment between the optical emitters/detectors and the earbud housing 16. This effect may be similar to that observed in "integrating spheres" commonly used for quantifying the lumen output of an optical source. Namely, because the light from the optical emitter 24 may be substantially isotropic and not focused, there is less restriction on the alignment of the earbud housing and earbud cover with respect to the optical emitter 24 or optical detector 26.

Referring now to FIGS. 7A-7B, a light guiding earbud 30, according to some embodiments of the present invention, includes a base 50, and an earbud housing 16 extending outwardly from the base 50 that is configured to be positioned within an ear E of a subject. The earbud housing 16 is formed from translucent material such that light can pass therethrough and forms a light-guiding region 19. The earbud housing 16 is in acoustical communication with a speaker 22 and includes at least one aperture 34a through which sound from the speaker 22 can pass. A pair of optical detectors 26 are secured to the base 50 but are not surrounded by the earbud housing 16, as illustrated.

The earbud housing 16 includes a flexible optical emitter 24 integrally formed within the housing 16, as illustrated. The optical emitter 24 is flexible such that it may be positioned around the earbud in an earbud form-factor. The flexible optical emitter 24 is configured to be conformable to an earbud shape and configuration. The flexible optical emitter 24 may be in, near, or part of the earbud housing 16, cladding material 21, or housing 16. In some embodiments, the flexible optical emitter 24 may be part of a flexible optical circuit inserted into an earbud 30.

The optical detectors 26 positioned outside the earbud housing 16 of the earbud 30 of FIGS. 7A-7B collect scattered light from an ear originating from inspection light 111 generated by the flexible optical emitter 24. The flexible optical emitter 24 may be mounted to the earbud base 50 through one or more electrical connectors 24a. In some embodiments, these may be soldered, wired, or detachable connectors. In some embodiments, the flexible optical emitter 24 may include a flexible optical detector. In some embodiments, the flexible optical emitter 24 may be part of a flexible optical circuit comprising the form-factor of 24 shown in FIGS. 7A-7B, where the flexible optical circuit may include one or more optical emitters and detectors as well as amplifiers, microprocessors, wireless circuitry, and signal conditioning electronics. In some embodiments, the flexible optical circuit may include a complete chipset for physiological and environmental detection and for wired/wireless transfer of data to a remote location. For example, these flexible devices may include an organic LED (OLED) and an organic optical detector circuit. This embodiment may be useful for generating a diffuse light beam towards the ear region and for detecting a diffuse optical scatter response from the ear region. In some embodiments, the emitter and detector on the flexible optical emitter 24 may be a traditional light-emitting diode (LED) and photodetector (PD) integrated onto a flexible printed circuit board. In other embodiments, transparent solid state optical emitters, detectors, or switches may be used. For example, an electrically controlled liquid crystal matrix may be embedded within an earbud, covering the flexible optical emitter 24. This may allow localized control of light flow to selected areas from/to the earbud going towards/away-from the ear. Additionally, this may allow localized control of light wavelength to selected areas.

Referring now to FIGS. 8A-8B, a light guiding earbud 30, according to some embodiments of the present invention, includes a base 50, an earbud housing 16 extending outwardly from the base 50 that is configured to be positioned within an ear of a subject, and a cover 18 that surrounds the earbud housing 16. The earbud housing 16 is in acoustical communication with a speaker 22 and includes at least one aperture 34a through which sound from the speaker 22 can pass. The cover 18 includes at least one aperture 34b through which sound from the speaker 22 can pass. The cover 18 includes a cladding material 21 on the outer surface 18a thereof, except at end portion 18f, as illustrated. In the illustrated embodiment, there is no cladding material on the cover inner surface 18b. The housing 16 is in contact with the cover inner surface 18b and serves as a cladding layer to define the light guiding region 19. The cover 18 with the illustrated cladding material 18c serves as a light guide that delivers light from the optical emitters 24 into an ear canal of a subject through cover end portion 18f. The cover 18 also collects light through end portion 18f and delivers the collected light to the optical detectors 26. Various configurations and arrangements of optical emitters and detectors may be utilized in accordance with embodiments of the present invention.

In the illustrated embodiment of FIGS. 8A-8B, to reduce the risk of the inspection light 111 interrogating and saturating the optical detectors 26, a bottom portion 16a of the earbud housing 16 includes a light blocking region that blocks light from passing therethrough. This light blocking region 16a may be a black-painted region, an optically opaque region, or a material or structure that blocks light transmission. The illustrated configuration of the earbud housing 16 and bottom portion 16a may help confine inspection light 111 generated by the optical emitters 24 within the light-guiding layer (i.e., 19), guiding this light towards the ear region through the end portion 18f of the earbud 30.

Figure 8C:
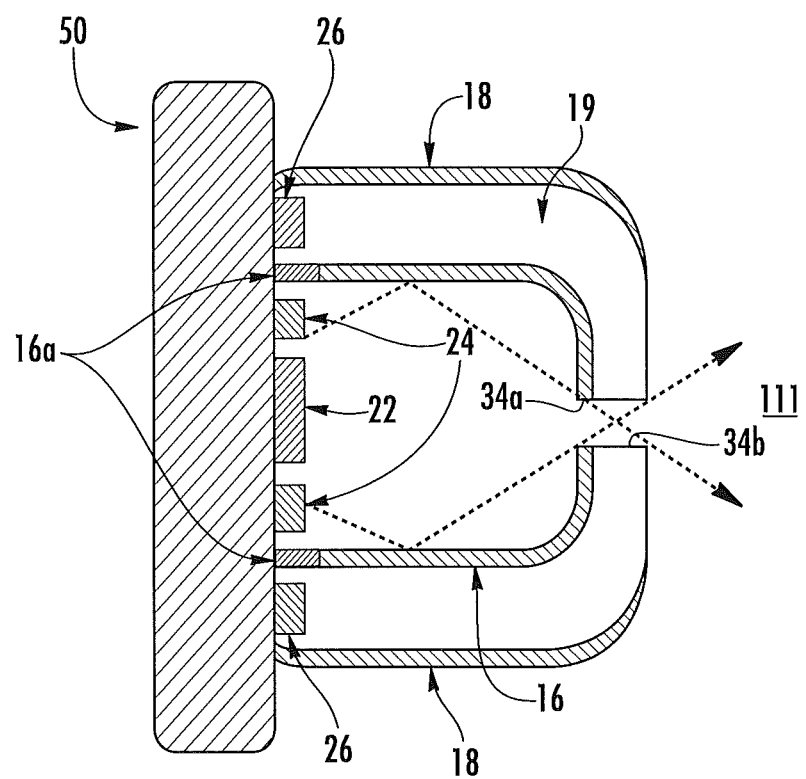
FIG. 8C is a side section view of a light-guiding earbud for a headset, according to some embodiments of the present invention.

In some embodiments, as illustrated in FIG. 8C, the earbud housing 16 may be at least partially reflective to scatter light within the cavity defined by the earbud housing 16. In such case, the optical energy 111 may exit the earbud 30 through apertures 34a, 34b in the housing 16 and cover 18. An advantage of this configuration is that light 111 can be focused on a particular region of the ear where a particular physiological activity may be located. Also, this configuration may reduce unwanted optical signals from regions that may not be relevant to the physiological activity of interest. Although FIG. 8C shows the apertures 34a, 34b positioned toward the tympanic membrane, the apertures 34a, 34b may be located at one or more other locations about the earbud 30. For example, an aperture may be formed in the housing 16 and cover 18 at the location where the earbud 30 contacts the antitragus of an ear to allow optical energy 111 to interrogate the antitragus region of the ear.

Figure 8D:
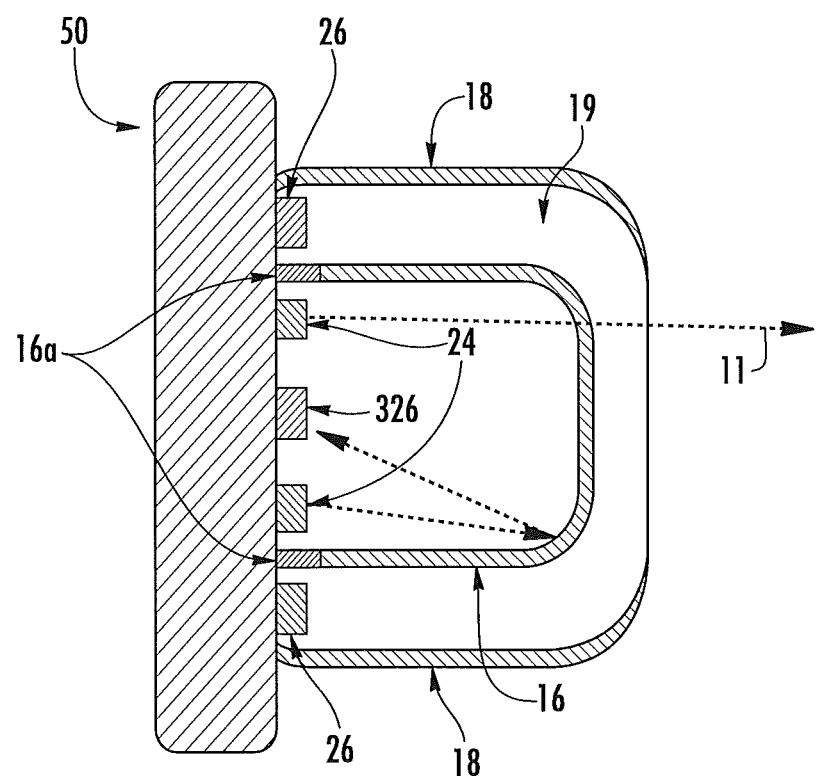
FIG. 8D is a side section view of a light-guiding earbud for a headset, according to some embodiments of the present invention.

In some embodiments, as illustrated in FIG. 8D, the earbud housing 16 may contain a material that reflects one or more wavelengths of light and transmits one or more wavelengths of light. For example, the earbud housing 16 may be comprised of a polymer, plastic, glass, composite material, or resin that reflects visible wavelengths and transmits IR wavelengths. Exemplary materials include color absorbing materials, such as organic dyes, found in photographic film. Alternatively, the earbud housing 16 may include an optical filter region, such as a Bragg filter or other optical filter layer deposited on one or more sides of the housing region. If an optical detector 26' is configured to measure visible wavelengths only, then the optical energy detected by optical detector 26' may consist primarily of optical energy scattered from the earbud housing 16, and the optical energy detected by the optical detectors 26 may consist of optical energy scattered from the ear region. This configuration may be useful because the signal from the optical detector 26' may represent motion noise which may be removed from the signal derived from the optical detectors 26, which may contain physiological information and motion noise.

Figure 9A:
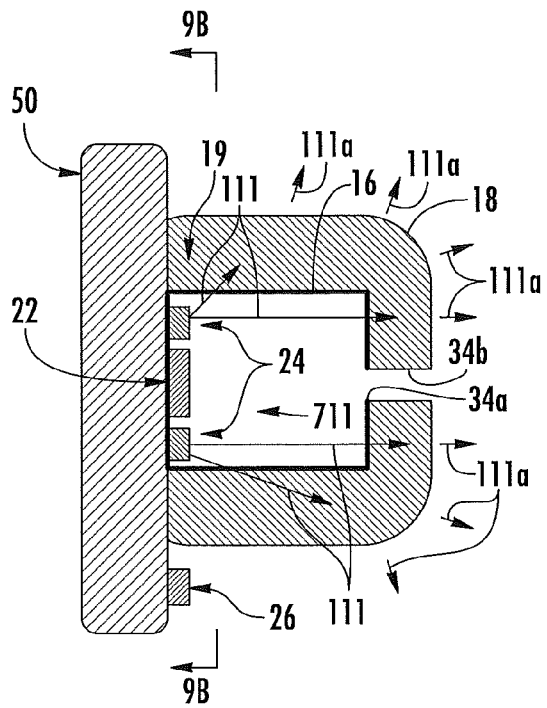
FIG. 9A is a side section view of a light-guiding earbud for a headset, according to some embodiments of the present invention.
Figure 9B:
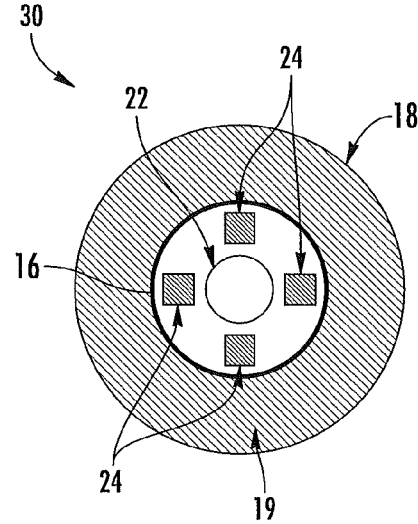
FIG. 9B is a cross-sectional view of the earbud of FIG. 9A taken along lines 9B-9B.

Referring now to FIGS. 9A-9B, a light guiding earbud 30, according to some embodiments of the present invention, includes a base 50, an earbud housing 16 extending outwardly from the base 50 that is configured to be positioned within an ear of a subject, and a cover 18 surrounding the earbud housing 16. The earbud housing 16 is in acoustical communication with a speaker 22 and includes at least one aperture 34a through which sound from the speaker 22 can pass. The cover 18 includes at least one aperture 34b through which sound from the speaker 22 can pass. A pair of optical emitters 24 are secured to the base 50 and are surrounded by the earbud housing 16, as illustrated. An optical detector 26 is secured to the base 50 and is not surrounded by the earbud housing 16, as illustrated. The cover 18 serves as a light guide that delivers light from the optical emitters 24 into an ear canal of a subject.

The light-guiding region 19 of the cover 18 is designed to diffuse light and/or to generate luminescence. In this embodiment, the light-guiding region 19 includes at least one optical scatter or luminescence region. The optical scatter or luminescence region may be located anywhere within the earbud in the optical path of the optical emitters 24, but preferably within or about the cladding layer itself. When inspection light 111 generated by the optical emitters 24 is scattered or by an optical scatter region, this light may form a more diffuse optical beam 111a that is more uniform across the earbud 30 than the inspection light 111 generated by the optical emitters 24. This diffused beam, having an intensity distribution being less sensitive to motion of the ear, may be useful in alleviating motion artifacts in the scattered light coming from the ear, such that the scattered light coming from the ear, measured by the optical detector 26, is more indicative of blood flow changes within blood vessels and less indicative of mouth movements and body motion. The optical scatter region within the light-guiding region 19 may be at least partially comprised of impurities or morphological differences within the light-guiding region. An example of such impurities may include point defects, volume defects, native defects, metallics, polymers, microspheres, phosphors, luminescent particles, air pockets, particles, particulate matter, and the like. An example of morphological differences may include density variations, roughness, air pockets, stoichiometry variations, and the like. As a specific example, the light-guiding region 19 may comprise a transparent material, such as glass, a polymer, or silicone, and a luminescent impurity, such as a phosphor or luminescent polymer or molecule, may be integrated within the light-guiding region. This configuration may generate luminescence within the light-guiding region 19 in response to optical excitation from the optical emitters 24. In other embodiments, nanoscale fluctuations or impurities may be used to diffuse or manipulate light through the earbud. Examples of nanoscale fluctuations or impurities may include quantum dots, rods, wires, doughnuts, or the like.

Figure 9C:
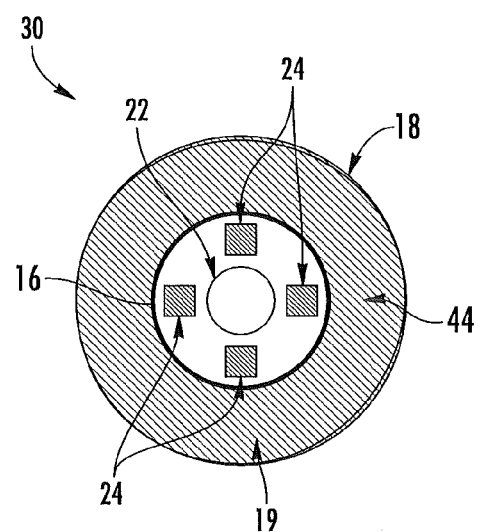
FIG. 9C illustrates luminescent particles within the earbud cover of FIGS. 9A-9B, according to some embodiments of the present invention.
Figure 9D:
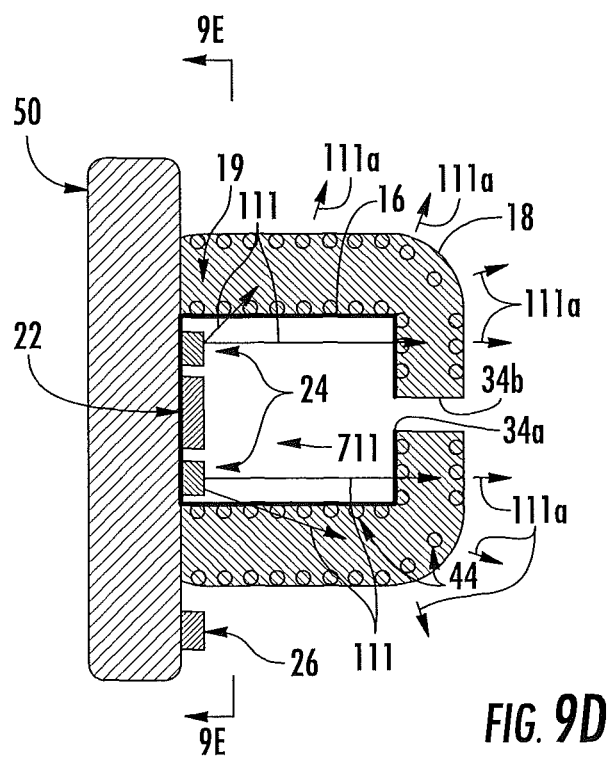
FIG. 9D is a side section view of a light-guiding earbud for a headset, according to some embodiments of the present invention.
Figure 9E:
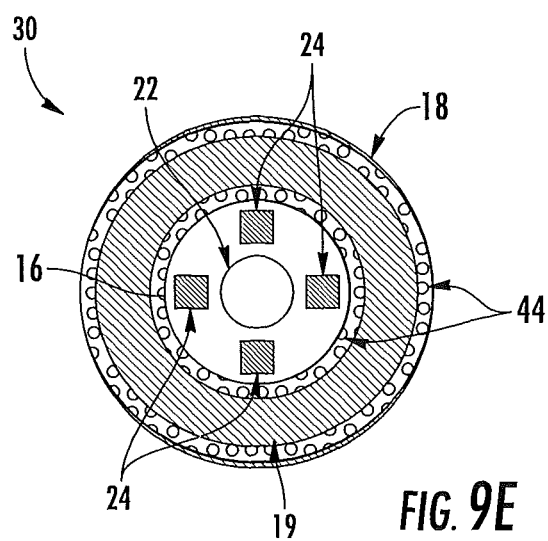
FIG. 9E is a cross-sectional view of the earbud of FIG. 9D taken along lines 9E-9E.

FIG. 9C illustrates an exemplary homogeneous distribution of luminescent particles 44, such as phosphors, embedded within the earbud cover 18, according to some embodiments of the present invention. FIGS. 9D-9E illustrate an exemplary distribution of luminescent particles 44, such as phosphors, where the particles are distributed near one or more surfaces of the earbud cover 18, according to some embodiments of the present invention.

In another embodiment, an optical scatter or luminescent region may be at least partially located in a separate region from the light-guiding region 19, such as a coating, that may be in physical contact with the light-guiding region 19.

In another embodiment, the optical scatter region or luminescent region may include multiple layers of light-guiding material having at least one dissimilar optical property, such as a dissimilar index of refraction, transparency, reflectivity, or the like. In another embodiment, the optical scatter region may include one or more patterned regions having at least one dissimilar optical property.

In another embodiment, the optical scatter or luminescent region may be distributed at select locations throughout the earbud.

Figure 10:
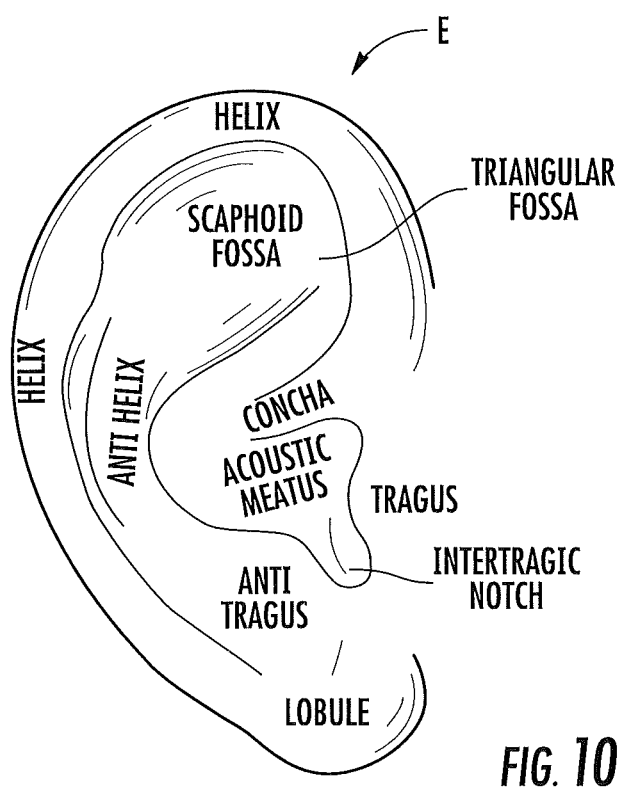
FIG. 10 illustrates various anatomy of a human ear.

FIG. 10 illustrates relevant anatomy of a human ear E. Blood vessels are located across the ear, but it has been discovered that photoplethysmography (PPG) signals are the strongest near the antitragus, tragus, lobule, and portions of the acoustic meatus, and the ear canal. The antitragus is a particularly attractive location for photoplethysmography because a strong PPG signal can be derived with minimal motion artifacts associated with running and mouth motion.

Referring now to FIGS. 11A-11B, a light guiding earbud 30, according to some embodiments of the present invention, includes a base 50, an earbud housing 16 extending outwardly from the base 50 that is configured to be positioned within an ear of a subject, and a cover 18 surrounding the earbud housing 16. The earbud housing 16 is in acoustical communication with a speaker 22 and includes at least one aperture 34a through which sound from the speaker 22 can pass. The cover 18 includes at least one aperture 34b through which sound from the speaker 22 can pass. The cover 18 serves as a light guide for directing light into an ear of a subject and defines a light-guiding region 19. The illustrated earbud 30 is configured to focus light towards the antitragus of the ear of a human. In the illustrated embodiment, there is no cladding material on the outer surface 18a or inner surface 18b of the cover 18. Air serves as a cladding layer at the outer surface 18a and the housing 16 serves as a cladding layer at the inner surface 18b. Air may serve as a sufficient cladding layer due to the index of refraction difference between air and the light guiding layer. Namely, the index of refraction of the light-guiding layer 19 may be more than that of air.

A sensor module 70 is located near the earbud periphery, as illustrated. This sensor module 70 is shown in more detail in FIGS. 12a-12B, and is described below. Three benefits of locating the sensor module 70 near the periphery of the light-guiding earbud 30 are: 1) PPG signals near the antitragus are less corrupted by motion artifacts than are PPG signals in other blood-vessel-rich regions of the ear; 2) the sensor module 70 may be designed somewhat independently of the earbud 30, liberating earbud comfort maximization from PPG signal maximization; and 3) because design constraints may be liberated, sensors need not be located in the acoustic cavity (i.e., within the earbud housing 16), allowing sound to pass through the acoustic orifices 34a, 34b with minimal interference. In this embodiment, it may be beneficial to incorporate lenses within the cover 18, similar to the lenses 18L of FIG. 6. It may be beneficial to extend the light-guiding region 19 of the cover 18 near the location where the earbud 30 rests near the antitragus. This light-guide extension 19a serves as an additional light-coupling region and may improve optical coupling from the light-guiding region 19 to an ear region and/or improve optical coupling from an ear region to the light-guiding region 19, including the antitragus and portions of the acoustic meatus. This is because this extended light-guiding region 19a may provide skin contact between the light guiding layer 19 and the skin, providing better optomechanical stability and optical coupling. In this embodiment, light may couple into the extended light-guiding region 19a, from an optical emitter 24, and into the ear region. Similarly, light may couple from the ear region, into the extended light-guiding region 19a, and to the optical detector 26. This extended light-guiding region 19a may appear as a bulb or lens near the bottom of the earbud cover 18.

FIGS. 12A-12B illustrate respective opposite sides of a sensor module 70 that may be located near the periphery of an earbud 30, for example as illustrated in FIGS. 11A-11B, according to some embodiments of the present invention. Sensor module 70 may include a number of electronic components capable of converting various forms of energy into an electrical signal and digitizing the signal. For example, the sensor module 70 may include light-emitting diodes, optical sensors, accelerometers, capacitive sensors, inertial sensors, mechanical sensors, electromagnetic sensors, thermal sensors, nuclear radiation sensors, biological sensors, and the like. In some embodiments, the optical emitters of this invention may be a combination of side-emitting, edge-emitting, or surface-emitting light-emitting diodes (LEDs) or laser diodes (LDs).

In the illustrated embodiment of FIGS. 12A-12B, the sensor module 70 includes two sets of optical emitters 24a, 24b. The first set of optical emitters 24a may be side-emitters (or edge-emitters) that are located at the top of the module 70 and direct light towards the earbud tip (e.g., cover end portion 18f, FIG. 8A) and towards the acoustic meatus and/or ear canal of the ear. The second set of optical emitters 24b may be located near the middle of the module 70 and may direct light in a beam that is largely perpendicular to that of the side-emitters 24a. In this particular embodiment, a single optical emitter 24b is shown mounted on a circuit board 70c such that this optical emitter 24b directs light towards the antitragus, which is located largely perpendicular to the acoustic meatus.

The optical energy generated by these optical emitters 24a, 24b may be scattered by blood vessels in the ear. This scattered light may be at least partially captured by the optical detectors 26. This light may be digitized by an optical detector 26 itself or with other circuitry on the sensor module circuit board 70c. The light-guiding design of the aforementioned light-guiding earbuds 30 may direct light towards each of these detectors 26. For example, this may be accomplished via the light-guiding earbud 30, wherein a lens (e.g., 18L, FIG. 6) facilitates inspection light coupling from the optical emitters 24 into the ear region and facilitates scattered light coupling to the optical detectors 26 from the ear region. Additional sensor components 27a, 27b may be used to measure an orthogonal energy component, facilitate sensor analysis, and thus help generate physiological assessments. For example, sensor components 27a, 27b may be thermal sensors for measuring the temperature of the inner ear (using the thermal sensors 27a facing the ear region) with respect to the outer ear (using the thermal sensor 27b facing away from the ear region). By subtracting the two measured digitized temperatures from these two sensors 27a, 27b, an indication of heat flow from the ear can be generated. This temperature differential may be mathematically related to metabolic rate. For example, this temperature differential may be directly proportional metabolic rate. These temperature sensors may include thermistors, thermopiles, thermocouples, solid state sensors, or the like. They may be designed to measure thermal conduction, convection, radiation, or a combination of these temperature components.

The earbud-facing side (FIG. 12B) of the sensor module 70 may include sensors that do not need to be located on the antitragus-facing side of the sensor module. For example, one or more inertial sensors 27c may be located on the earbud-facing side (FIG. 12B) of the sensor module 70. In a particular embodiment, the inertial sensor 27c may be a 3-axis accelerometer, and because this sensor does not need to optically couple with the ear region, a better use of sensor real estate may be to locate this sensor on the earbud-facing side of the sensor module 70. Additional optical emitters 24a, 24b may be located on the earbud-facing side to facilitate an optical noise reference. Namely, as the person wearing the earbud module 30 moves around, the interrogation light generated by the optical emitters 24a, 24b may be scattered off the earbud and be detected by optical detectors 27d. This scattered light intensity, phase, and/or frequency due to body motion may be proportional to the motion-related component of the scattered light intensity from the ear region. The motion-related component is the component due to the physical motion of the ear and not the component related to blood flow. Thus, the optical scatter signal collected by the detectors 27d may provide a suitable noise reference for an adaptive filter to remove motion artifacts from the scattered light from the ear region, generating an output signal that is primarily related to blood flow (which may be the desired signal). In the same token, the scattered light reaching the optical detectors 27d may be used to generate a measure of activity. The intensity, phase, and frequency of this scattered light may be related to physical activity. Sinusoidal variations of the heart rate waveform may be counted digitally, by identifying and counting crests and peaks in the waveform, to generate an effective step count. Embodiments of the present invention, however, are not limited to the illustrated location of components in the sensor module 70. Various types and orientations of components may be utilized without limitation.

Figure 19:
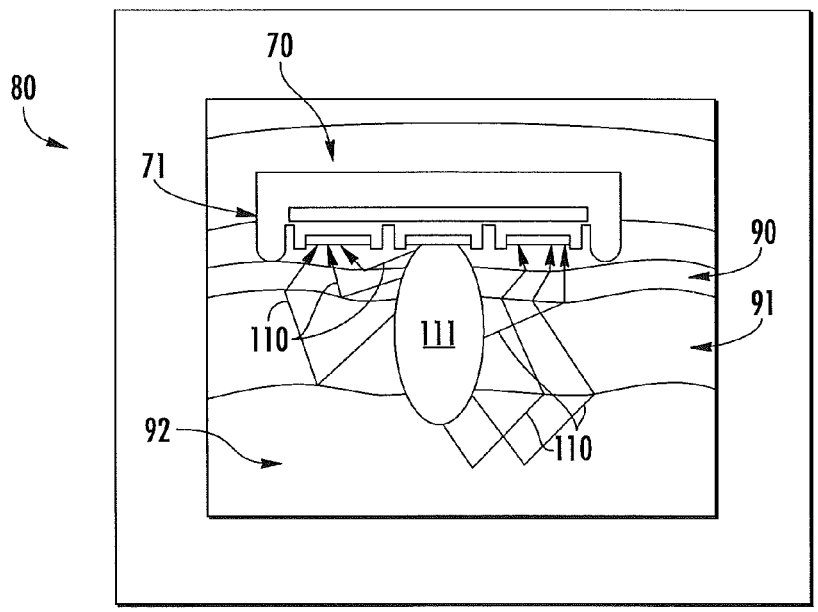
FIG. 19 illustrates the optical interaction between the sensor module of FIGS. 12A-12B and the skin of a subject.

FIG. 19 illustrates the optical interaction between the sensor module 70 of FIGS. 12A-12B and the skin of a subject. The sensor module 70 is shown in a reflective pulse oximetry setup 80 where reflected wavelengths 110 are measured, as opposed to measuring transmitted wavelengths. The optical emitter and optical detector wavelengths for pulse oximetry and photoplethysmography may include ultraviolet, visible, and infrared wavelengths. In the illustrated embodiment, an optical source-detector assembly 71 is integrated into sensor module 70 to generate optical wavelengths 111 and monitor the resulting scattered optical energy 110. The optical source-detector assembly 71 contains one or more optical sources emitting one or more optical wavelengths, as well as one or more optical detectors detecting one or more optical wavelengths.

The epidermis 90, dermis 91, and subcutaneous 92 layers of skin tissue are shown in FIG. 19 for reference. The scattered optical energy 110 may be modulated in intensity by changes in blood flow in the blood vessels, changes in physical motion of the body, respiration, heart rate, and other physiological changes. In some cases, the scattered optical energy may be luminescent energy from the skin, blood, blood analytes, drugs, or other materials in the body.

As previously described, the optical scatter signal collected by the detectors 27d may provide a suitable noise reference for an adaptive filter to remove motion artifacts from the scattered light from the ear region, generating an output signal that is primarily related to blood flow (which may be the desired signal). This is because light detected by these detectors would come from light that has not been scattered by a physiological region but rather light that has been scattered from a region of the associated earpiece that may move along with the ear. Thus, the scattered light reaching the optical detectors 27d may be used to generate a measure of activity.

Figure 13:
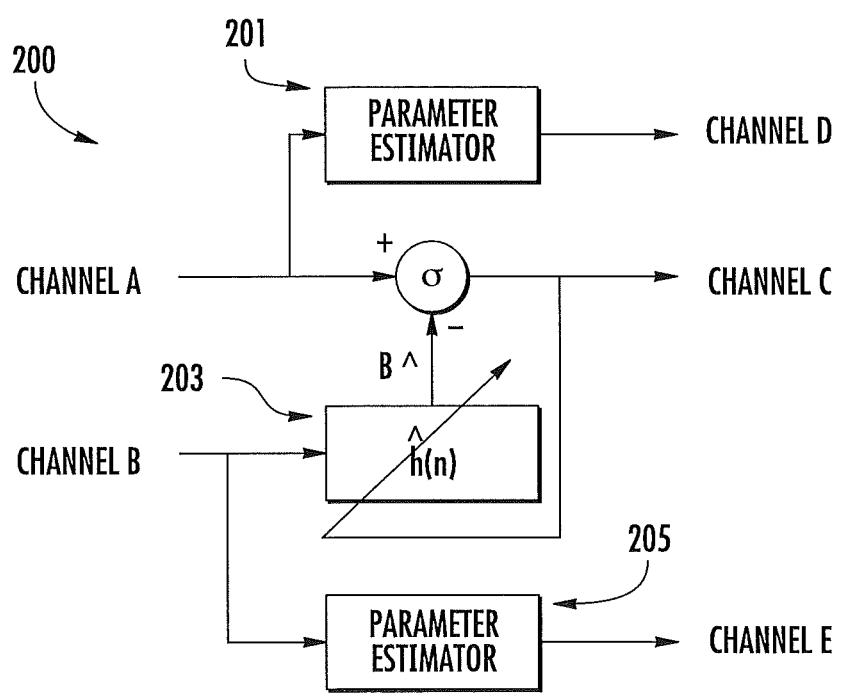
FIG. 13 illustrates an adaptive filter and noise source for removing noise from a noisy physiological signal, according to some embodiments of the present invention.
Figure 14A:
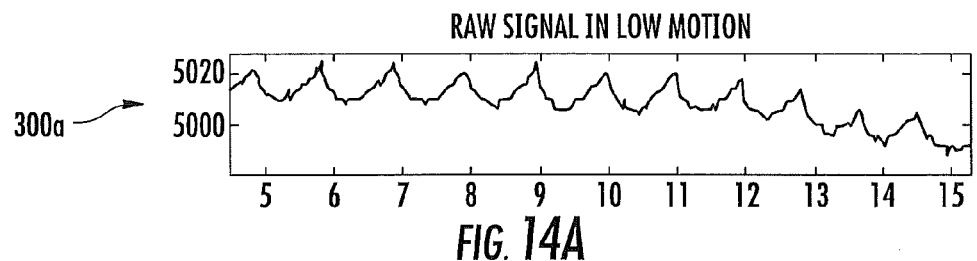
FIGS. 14A-14D are respective graphs of time-dependent data collected from a light-guiding earbud worn by a person, according to some embodiments of the present invention.
Figure 14B:
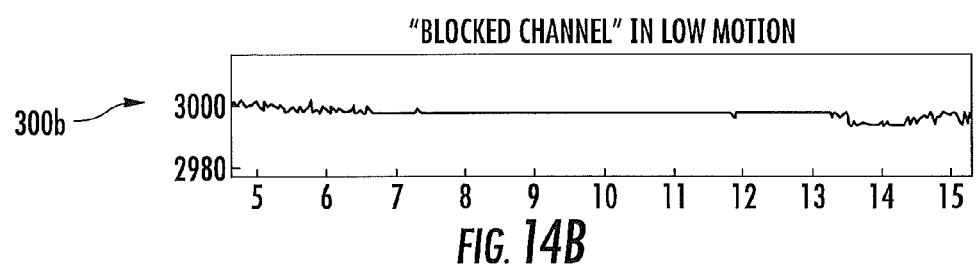
Figure 14C:
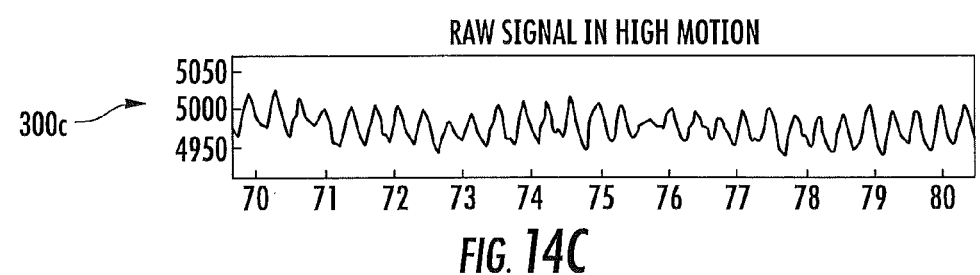
Figure 14D:
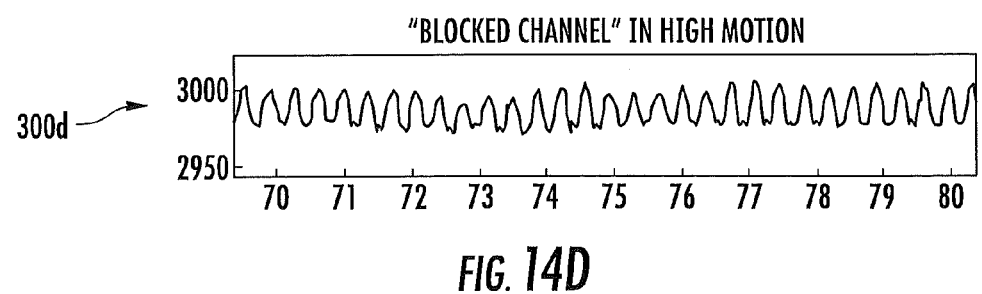

FIG. 13 illustrates the basic configuration of an adaptive noise cancellation scheme 200 for extracting a physiological signal from noise. The two types of sensor inputs are represented by the terms "Channel A" and "Channel B". Channel A refers to inputs from sensors that collect physiological information plus noise information, and Channel B refers to inputs from sensors that collect primarily (or substantially) noise information. Channel B information is passed through an electronic filter 203 whose properties are updated adaptively and dynamically. The filter 203 properties are updated to minimize the difference between Channel A and the post-processed Channel B, denoted as B^. In this way, noise is removed from Channel A and Channel C contains predominantly physiological information from which parameters such as blood flow, heart rate, blood analyte levels, breathing rate or volume, blood oxygen levels, and the like may be calculated. It is important to note that the Channel A information can still be useful despite the presence of noise, and the noise information may still be utilized for the computation of relevant parameters. For instance, the residual noise information in Channel A may be extracted by a parameter estimator 201 and the output in Channel D may be one or more activity assessments or the like. Similarly, the raw noise channel, Channel B, may be post-processed by a parameter estimator 205 to extract activity assessments for Channel E. Activity assessments may include exertion, activity level, distance traveled, speed, step count, pace, limb motion, poise, performance of an activity, mastication rate, intensity, or volume, and the like. The noise cancellation scheme 200 may be integrated into the firmware of a microprocessor or the like.

Although the embodiment of FIG. 13 for cancelling motion noise has been presented for an earbud configuration, this does not limit the invention to earbuds. An element of the adaptive noise cancellation scheme 200 for cancelling motion noise with an optical noise source may be that the optical detectors (such as 27d) are configured such that they do not receive scattered light from a physiological region while the detectors are simultaneously receiving scattered light from a region that is moving in synchronization with the physiological region. Even the slightest physiological signal existing in the optical noise reference of Channel B may prevent the adaptive filter from working properly such that the physiological signal may inadvertently be removed altogether by the filter 203. Furthermore, although the noise source Channel B is described as an optical noise source, other forms of energy may be used in this invention. Namely, any inertial sensor input may constitute the input for Channel B. More specifically, a sensor for measuring changes in capacitance along the earbud with respect to the ear may provide an inertial noise reference without also measuring physiological information. Similarly, an accelerometer may provide an inertial noise reference without also measuring physiological information. An inductive sensor may also provide an inertial noise reference without also measuring physiological information. For each noise source, a defining element may be that the noise source may be configured to measure physical motion only (or mostly) and not physiological information (such as blood flow, blood oxygen, blood pressure, and the like). The utility of an optical noise source is that because the optical signal Channel A and the optical noise Channel B have the same linearity response, the adaptive filter scheme 200 may be more effective than the case where the signal and noise channels operate via different forms of sensed energy. For example, the response linearity characteristics of an accelerometer sensor in response to inertial changes may not be the same as the response linearity characteristics of an optical sensor.

The adaptive noise cancellation scheme 200 for cancelling motion noise with an optical source (specifically an infrared LED) has been demonstrated in the laboratory, with a human wearing a light-guiding earbud while resting, jogging, and running over a treadmill, and various data summaries 300a-300d are presented in FIGS. 14A-14D. The data was recorded by a chip and memory card embedded in an earbud 30, having electrical connectivity with the sensor module 70 within the earbud 30. The raw signal in low motion 300a and raw signal in high motion 300c may be equated with the signal of Channel A of FIG. 13. Similarly, the "blocked channel" in low motion 300b and "blocked channel" in high motion 300d may be equated with Channel B of FIG. 13. In this experiment, the "block channel" consisted of an optical noise source, wherein the optical noise source included an optical emitter-detector module such as 70 of FIGS. 12A-12B. However, instead of being exposed to the ear, the optical emitter-detector module was covered with a layer of clear silicone that was then covered by black tape to prevent light from the emitter (such as 24a and 24b) from reaching the ear. Thus, scatter from the black tape was scattered back to the emitter-detector module through the silicone and sensed as motion noise by the detectors (such as 26 and 27d). In a sense, for this configuration, the optical channel to the human ear is "blocked", hence the term "blocked channel". The purpose of the clear silicone below the black tape was to: 1) provide an unobstructed, transparent optical scatter path for the IR light and 2) provide motion sensitivity similar to that of human skin, as silicone has a vibration response that may be similar to that of human skin.

FIGS. 14A-14D show that the raw signal in low motion 300a indicates blood flow pulses which can be translated as heart rate. This is because each blood flow pulse represents one heart beat. However, the raw signal in high motion 300c indicates measured mostly physical activity. This is evident by the fact that the high motion signal 300c matches the corresponding blocked channel signal 300d, and the blocked channel in high motion 300d was found to have a substantially identical beat profile with the measured steps/second of the runner.

Figure 15:
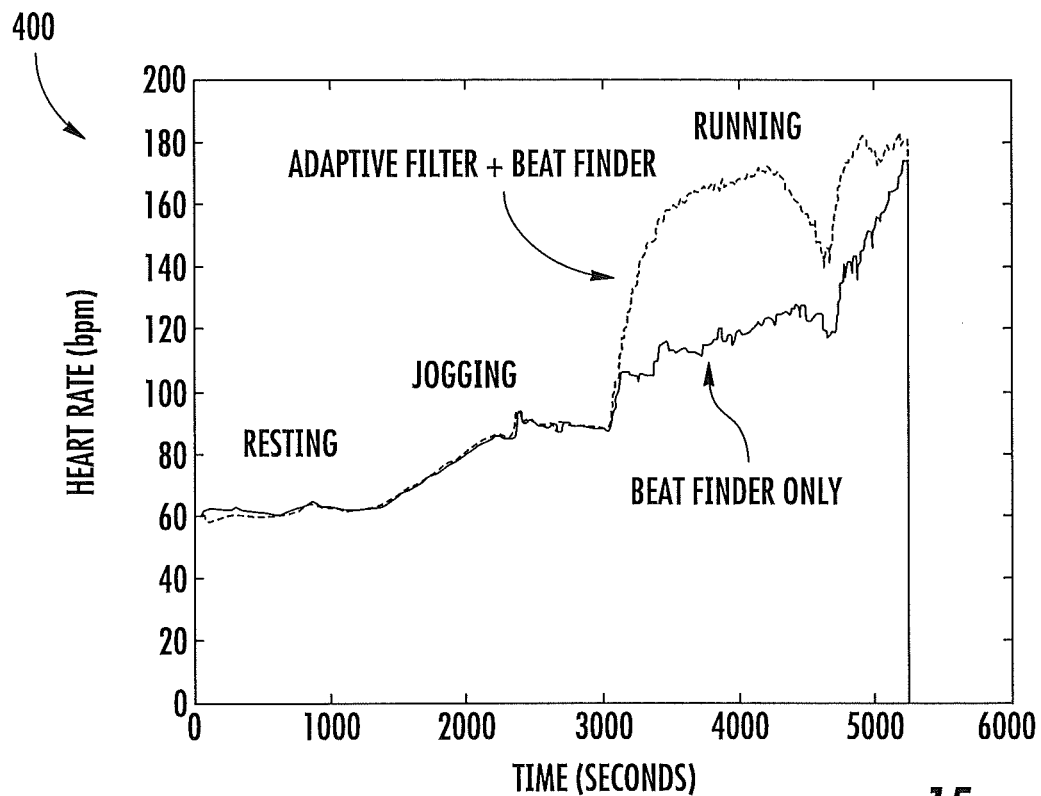
FIG. 15 is a graph of processed physiological signal data from a headset having one or more light-guiding earbuds, according to some embodiments of the present invention.

FIG. 15 is a graph of processed physiological signal data from a headset having one or more light-guiding earbuds 30, according to some embodiments of the present invention. Specifically, FIG. 15 shows the analysis results 400 of the data summaries 300a-300d presented in FIGS. 14A-14D of blood flow (y-axis) versus time (x-axis) following two data processing sequences to extract heart rate. One sequence incorporated the adaptive filtering process 200 of FIG. 13 as well as a beat finder processing step. The second sequence incorporated the beat finder processing step without the adaptive filtering process 200 of FIG. 13. The beat finder process counts each heart beat by monitoring the peaks and valleys of each pulse, such as the peaks and valleys shown in the graph 300a of FIG. 14A. As shown in FIG. 15, the beat finder was effective at measuring heart rate during resting and jogging. However, the beat finder alone was not sufficient for monitoring heart rate during running. This is because at high motion, the signal 300d (FIG. 14D) associated with footsteps is strong enough to overwhelm the smaller signal associated with heart rate, and so the motion-related contribution dominated the overall signal 300d. Thus, the beat finder cannot distinguish heart beats from footsteps. By employing the adaptive filtering process 200 (FIG. 13) before the beat finder process, the footstep motion artifacts during running were effectively removed from the sensor signal (Channel A of FIG. 13) such that the output signal (Channel C of FIG. 13) contained blood flow information with minimal motion artifacts. Thus, this output signal contained blood flow pulse signals that could then be "counted" by the beat finder to generate an accurate heart rate assessment.

Figure 16:
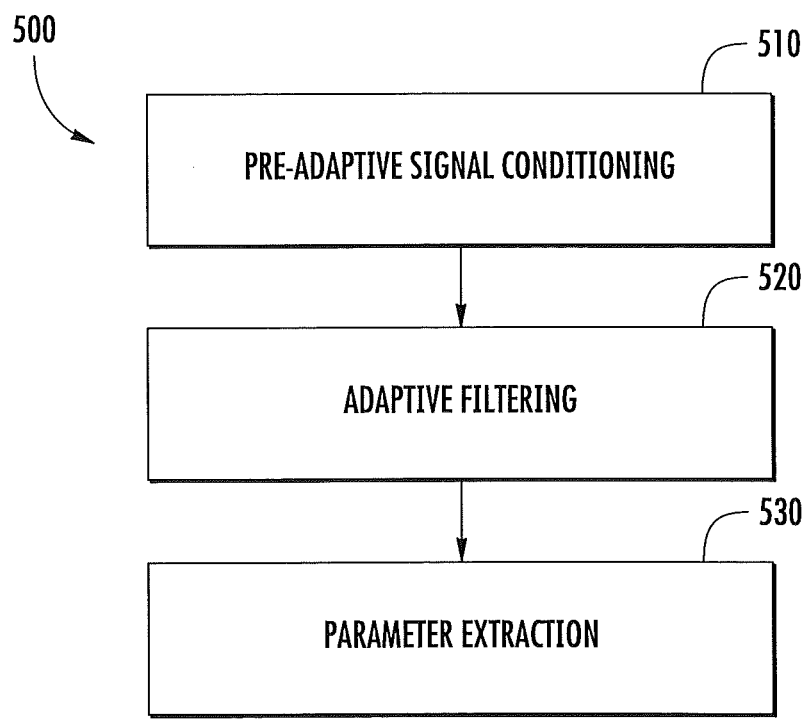
FIG. 16 is a flow chart of operations for extracting physiological information from headset sensor signals, according to some embodiments of the present invention.

In the specific analysis results 400 of FIG. 15, a beat finder was employed, following the adaptive filter process 200 of FIG. 13, to count heart beats. A more general method 500 for extracting physiological information from sensor signals in the midst of noise is illustrated in FIG. 16. The first block (block 510) represents the pre-adaptive signal conditioning stage. This process may utilize a combination of filters to remove frequency bands outside the range of interest. For example, a combination of band-pass, low-pass, and/or high-pass filters (such as digital filters) may be used. The second block (block 520) represents an adaptive filtering process such as the process 200 described in FIG. 13. This process may utilize the pre-conditioned signals from block 510 as inputs into an adaptive filter that reduces motion or environmental artifacts and noise in the primary data channel. The third block (block 530) represents the parameter extraction stage. This process may utilize a combination of signal conditioning filters in addition to peak finding (such as beat finding) algorithms to calculate properties of interest (e.g. heart rate, blood flow, heart rate variability, respiration rate, blood gas/analyte level, and the like). The method 500 of FIG. 16 may be encoded in the firmware of a microprocessor (or similar electronics) to facilitate real-time processing of physiological information.

Figures 17, 18:
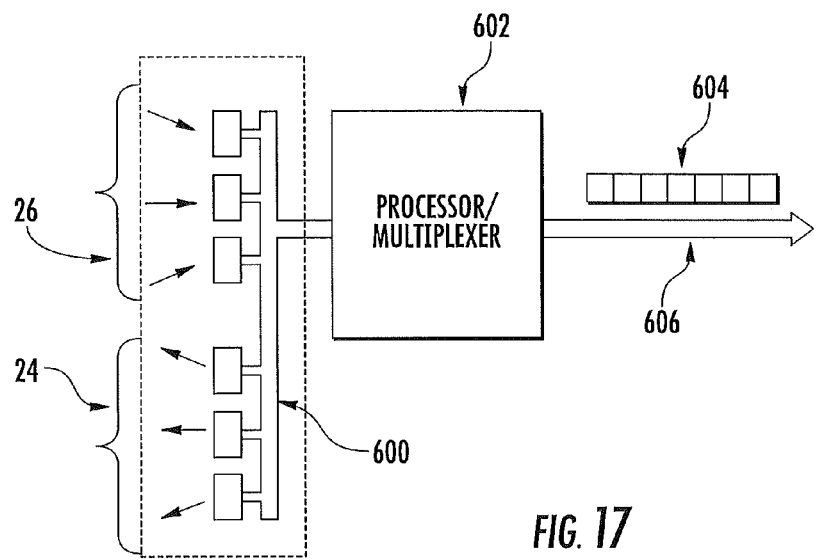
FIG. 17 is a block diagram that illustrates sensor signals being processed into a digital data string including activity data and physiological data, according to some embodiments of the present invention.
FIG. 18 illustrates a digital data string, according to some embodiments of the present invention.

FIG. 17 is a block diagram that illustrates sensor signals being processed into a digital data string including activity data and physiological data using the method 500 of FIG. 16, according to some embodiments of the present invention. Optical detectors 26 and optical emitters 24 may include digitizing circuitry such that they may be connected serially to a digital bus 600. Data from the detectors 26 may be processed by a processor/multiplexer 602 to generate multiple data outputs 604 in a serial format at the output 606 of the processor 602. In some embodiments, the processing methods may involve one or more of the methods described in FIGS. 13, 14A-14D, 15 and 16. The multiple data outputs 604 may be generated by the processor/multiplexer 602 by time division multiplexing or the like. The processor 602 may execute one or more serial processing methods, wherein the outputs of a plurality of processing steps may provide information that is fed into the multiplexed data outputs 604.

The multiplexed data outputs 604 may be a serial data string of activity and physiological information 700 (FIG. 18) parsed out specifically such that an application-specific interface (API) can utilize the data as required for a particular application. The applications may use this data to generate high-level assessments, such as overall fitness or overall health. Furthermore, the individual data elements of the data string can be used to facilitate better assessments of other individual data elements of the data string. As a specific example, the Blood Flow data string may contain information on the first and second derivatives of each blood pulse. This information may be processed from a PPG signal by running the adaptively filtered heart rate signal through a slope-finder algorithm (such as a differentiator circuit). In another example, the filtered PPG signal may be run through an integration circuit to estimate blood volume over each blood pulse. This information may then be used to assess blood pressure and blood oxygen levels more accurately than a direct measurement of blood pressure or blood oxygen levels.

In some embodiments of the invention, new methods of generating physiological assessment algorithms are enabled. These new methods may be achieved by measuring each data output of the data output string 604 in real time while an earbud user is also wearing one or more benchmark sensors. Principal component analysis, multiple linear regression, or other statistical or machine learning techniques can then be used to generate statistical relationships between the data outputs 604 and high level assessments measured simultaneously by the benchmark sensors. These benchmark sensors may measure aerobic fitness level, $VO_2$max, blood pressure, blood analyte levels, and the like. The relationships between the earbud sensor and benchmark sensor readings may be translated as algorithms embedded in the earbud, wherein each algorithm generates at least one assessment for the earbud user. In some cases, Bland-Altman plots of the earbud-derived assessment value versus the benchmark value may be used to judge the effectiveness of the algorithm, and this information may then feedback into improving the said earbud-derived assessment algorithm. Examples of these assessments may include aerobic fitness level, $VO_2$max, blood pressure, blood analyte levels (such as blood glucose, oxygen, carbon monoxide, etc.), and the like.

In some cases, it may be important to remove the effects of ambient optical noise from the physiological signal of a light-guiding earbud 30. In such cases, one or more optical detectors 26 may be configured to measure outdoor or ambient lighting, and this information may be fed back into the processor 602 (FIG. 17) to extract external optical noise from the physiological signal. For example, some optical detectors may be configured to measure light from the ear, whereas others may be configured to measure light from the ambient environment, such as sunlight, room light, headlights, or the like. This may be achieved by directing the optical detectors towards and away from the ear, respectively. In a specific example, the ambient light reaching the optical detectors 26 may generate an undesirable sinusoidal response on an optical detector that is configured to measure light from the ear. This undesirable sinusoidal noise response may be generated as an earbud user moves their head from side to side while running. Thus, Channel A of the adaptive filter 200 (FIG. 13) may include physiological information plus undesired ambient optical noise information. To remove this noise from the final output Channel C, the output of the optical detector configured to measure ambient optical noise may be an input (Channel B of FIG. 13) into the adaptive filter 200. In this way, ambient noise from Channel A may be removed to generate a mostly physiological signal in Channel C.

The optical detectors 26 and emitters 24 may be of multiple wavelengths, with the goal of providing specialized physiological information for each wavelength. Referring to FIG. 19, for example, violet or UV light may be used to measure motion-related aspects of the ear, as violet and UV light may not penetrate greatly through the skin of the ear. Green, red, and IR wavelengths may have deeper penetration and provide information on the blood vessels and blood analyte levels. Blue wavelengths may be particularly useful for gauging changes in the size of the blood vessels.

Embodiments of the present invention may be more generally applied to non-optical or mix-optical configurations. For example, one or more of the detectors 26 and emitters 24 may be mechanical, acoustical, electrical, gravimetric, or nuclear detectors and emitters, all providing physiological information to the processor 602 (FIG. 17). For example, an accelerometer or capacitor may be used as a detector 26 for the noise reference (Channel B) input of an adaptive filter running in real-time on the processor 602.

Figure 20:
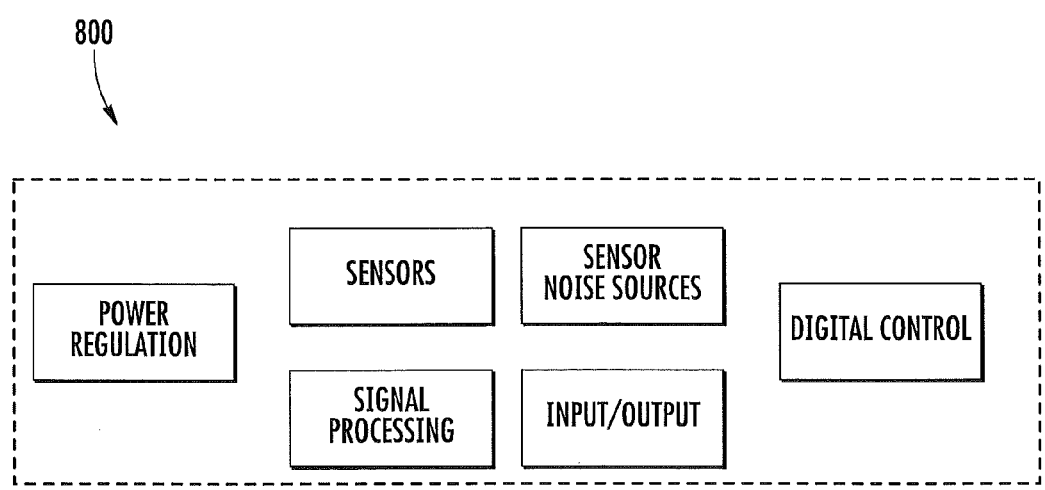
FIG. 20 illustrates a chipset for use in a headset, according to some embodiments of the present invention.

Referring to FIG. 20, a chipset 800 for use in light-guiding earbuds 30, according to some embodiments of the present invention, may include optical emitters, optical detectors, mechanical, acoustical, electrical, gravimetric, nuclear detectors, additional sensors, signal processing, power regulation, digital control, and input/output lines. The chipset 800 may include firmware for signal extraction and for generating physiological assessments from information derived from the sensors and noise sources. One benefit of the chipset configuration is that the chipset 800 may be fully or partially integrated and hence compact and scalable to a wide range of products. To be integrated with a light-guiding earbud 30, the chipset 800 may be aligned such that the sensor region has an exposed window to a subject's ear. For example, the chipset 800 may be attached to the earbud base 50 or an earbud sensor module 70 and aligned line-of-sight through an acoustic orifice of an earbud and/or through a transparent end portion of an earbud 30 (e.g., through end portion 18*f* of the earbud 30 of FIG. 8A-8B or 18*w* of FIGS. 4 & 5).

Figure 21:
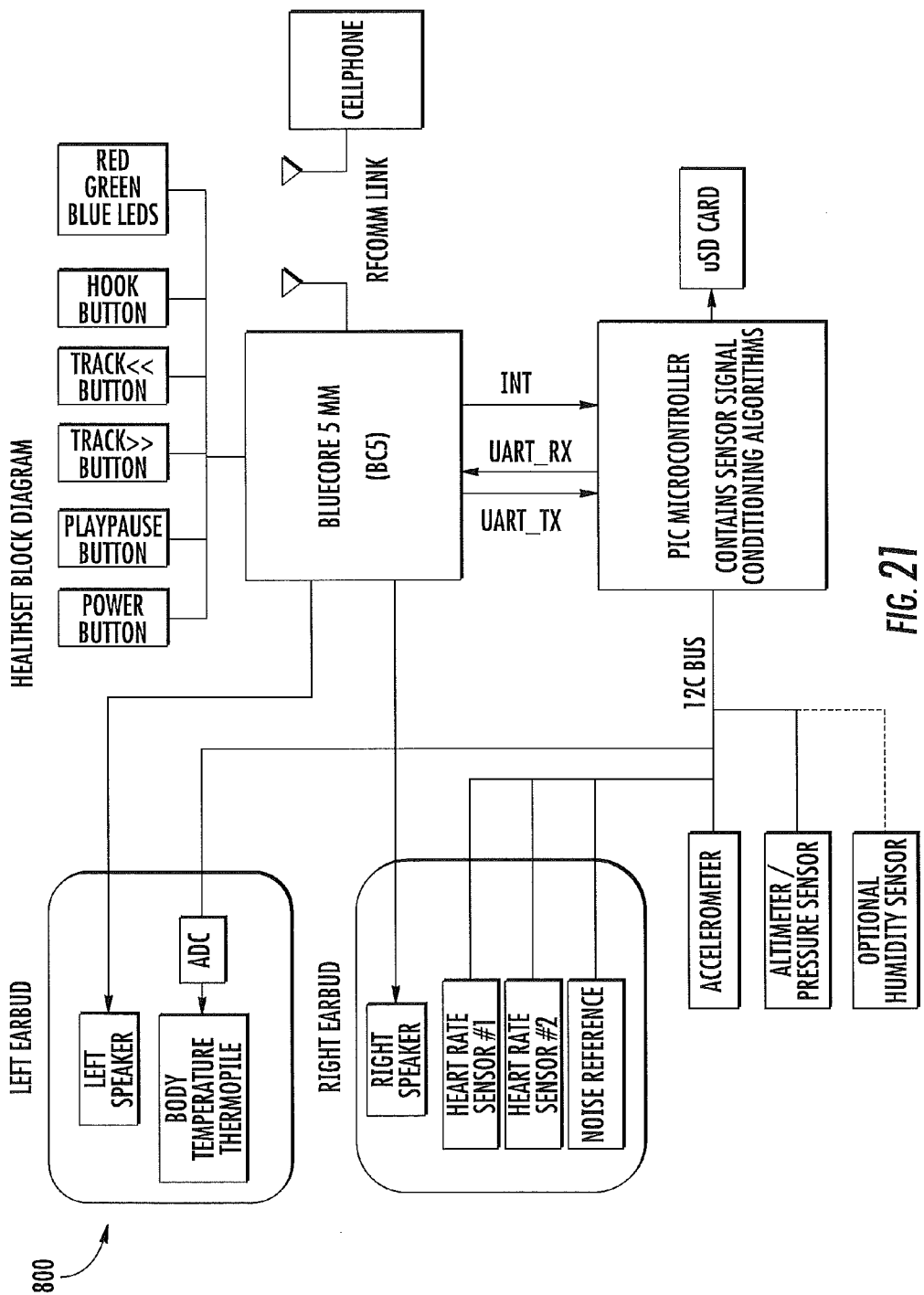
FIG. 21 illustrates a chipset for use in a stereo headset, according to some embodiments of the present invention.

A specific embodiment of a chipset 800 for a stereo headset, according to some embodiments of the present invention, is illustrated in FIG. 21. This stereo chipset 800 may be integrated into an electronic module that may be attached to a printed circuit board. In another configuration, this stereo chipset 800 may be integrated into 3 modules, wherein the right and left earbud sensors comprise two separate modules, embedded in right and left earbuds respectively, and wherein the remaining circuit elements comprise the main module.

Figure 22B:
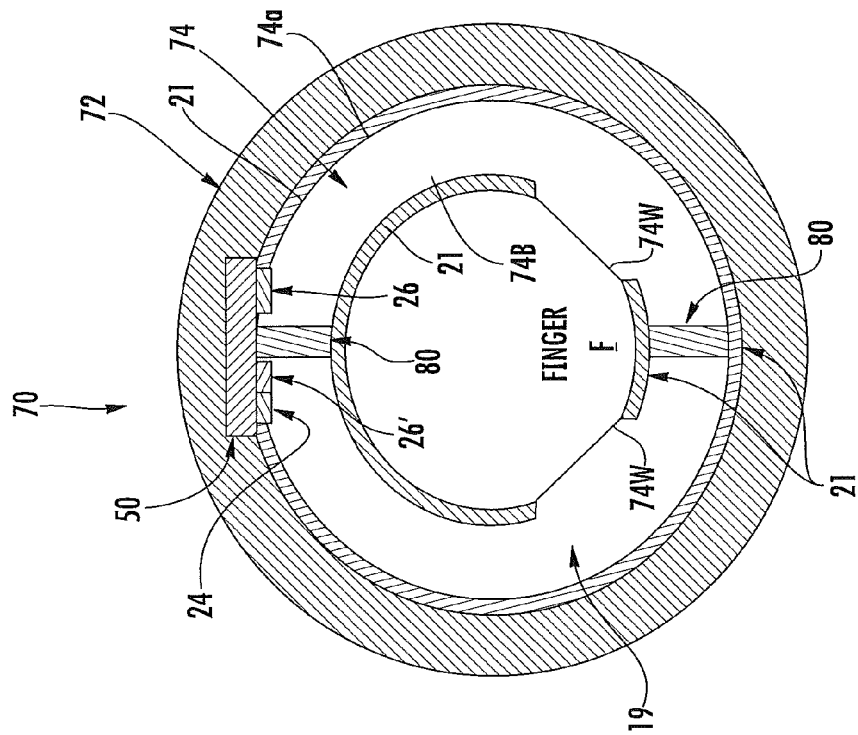
FIG. 22B is a cross-sectional view of the monitoring device of FIG. 22A taken along lines 22B-22B.
Figure 22A:
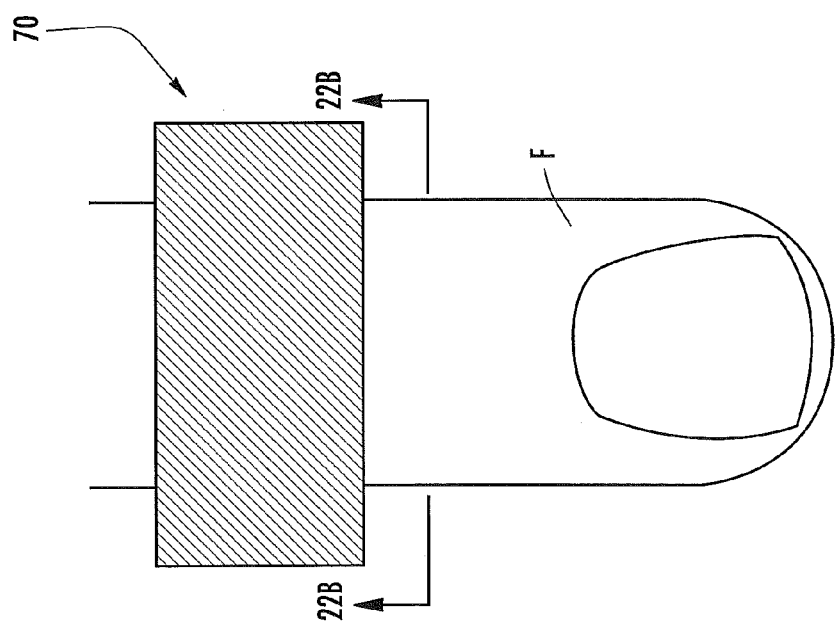
FIG. 22A is a top plan view of a monitoring device configured to be attached to finger of a subject, according to some embodiments of the present invention.

According to other embodiments of the present invention, monitoring devices with light-guiding regions may be configured to be attached to earlobes, fingers, toes, other digits, etc. For example, FIGS. 22A-22B illustrate a monitoring device 70 that is configured to fit over a finger F, for example, as a finger ring, according to some embodiments of the present invention. The illustrated monitoring device 70 includes a generally circular band capable of encircling a finger F of a subject, with a cylindrical outer body portion 72 and a generally cylindrical inner body portion 74 secured together in concentric relationship. The outer body portion may be formed from virtually any type of material and may have an ornamental configuration. In some embodiments, the outer body portion 72 may include a flex circuit containing various electronic components, such as a microprocessor, D/A converter, power source, power regulator, and the like. However, in some embodiments, the outer body portion 72 may not be required and the circular band of the monitoring device 70 includes only the inner body portion 74 secured to the base 50 (described below).

A base 50 is secured to the inner and outer body portions 74, 72 of the illustrated embodiment and may be similar to the base 50 described above with respect to FIGS. 3, 4A-4D, 5, 6, 7A-7B, 8A-8D, 9A-9B, and 11A-11B. The base 50 provides support for one or more sensors. In the illustrated embodiment, the base 50 supports an optical emitter 24, an optical detector 26, and an optical noise detector 26'.

The inner body portion 74 includes light transmissive material similar to that of the cover 18 described above with respect to FIGS. 3, 4A-4D, 5, 6, 7A-7B, 8A-8D, 9A-9B, and 11A-11B. In some embodiments, the inner body portion 74 is formed from a soft, resilient material, such as silicone, which deforms when a finger of a subject is inserted therethrough. However, various types of light transmissive materials may be utilized, without limitation.

A layer of cladding material 21 is applied to (or near) the outer surface 74a of the inner body portion 74 and a layer of cladding material 21 is applied to (or near) the inner surface 74b of the inner body portion 74, as illustrated, to define a light-guiding region 19. As such, the inner body portion 74 serves as a light guide that delivers light from the optical emitter 24 to the finger F of a subject at one or more predetermined locations and that collects light from the finger F and delivers the collected light to the optical detectors 26, 26'. In some embodiments, the cladding material 21 may be embedded within the inner body portion 74 adjacent to the outer surface 74a and inner surface 74b. In some embodiments, the outer body portion 72 may serve as a cladding layer adjacent to the inner body portion outer surface 74a.

In the illustrated embodiment, windows 74w are formed in the cladding material 21 and serve as light-guiding interfaces to the finger F. There may be any number of these windows, as may be required for sufficient optical coupling, and the windows 74w may include lenses such as those described above (e.g., lens 18L illustrated in FIG. 6), to focus light emitted by the optical emitter 24 onto one or more portions of a finger F and/or to focus collected light on the light detectors 26, 26'. Similarly, the windows 74w may include optical filters to selectively pass one or more optical wavelengths and reflect and/or absorb other optical wavelengths.

In the illustrated embodiment, the light-guiding region 19 includes light blocking members 80 that isolate light emitter 24 and light detector 26 from each other. In some embodiments, only a single light blocking member 80 may be utilized. For example, a single light blocking member 80 may be positioned between the light emitter 24 and light detector 26. By adding an additional blocking member 80, as illustrated, the only light reaching the optical detector 26 may be light passing through at least one portion of the finger.

In some embodiments, multiple light emitters 24 may be utilized. For example, light emitters of different wavelengths may be utilized. In some embodiments, multiple light detectors may be utilized that are configured to measure light at different wavelengths (e.g., light detectors 26 and 26' may be configured to measure light at different wavelengths). In this way, either optical detector may be configured to measure light mostly due to motion (such as finger motion) or to measure light mostly due to physiological processes and motion. For example, if the windows 74w incorporate IR-pass filters, visible light will not pass through the windows 74w and the light will be scattered to the photodetectors 26 and 26'. Or, if the two illustrated blocking regions 80 are in place, and if photodetector 26' is configured to measure only visible light and photodetector 26 is configured to measure only IR light, then only the photodetector 26' will detect scattered visible light. As this visible scattered light cannot reach the finger, the scatter intensity measured by optical detector 26' may be indicative of motion and not physiological activity.

Referring now to FIG. 23, a monitoring device 70', according to some embodiments of the present invention, may be configured to be attached to a body of a subject as a bandage or "band-aid". The illustrated monitoring device 70' includes an outer layer or body portion 72 and an inner layer or body portion 74 secured together, as illustrated. The outer body portion may be formed from virtually any type of material and may have an ornamental configuration. In some embodiments, the outer body portion 72 may include a flex circuit containing various electronic components, such as a microprocessor, D/A converter, power source, power regulator, and the like. However, in some embodiments, the outer body portion 72 may not be required and the monitoring device 70' includes only the inner body portion 74 secured to the base 50 (described below).

A base 50 is secured to the inner and outer body portions 74, 72 and may be similar to the base 50 described above with respect to FIGS. 3, 4A-4D, 5, 6, 7A-7B, 8A-8D, 9A-9B, and 11A-11B. The base 50 provides support for one or more sensors. In the illustrated embodiment, the base 50 supports an optical emitter 24, an optical detector 26, and an optical noise detector 26'.

The inner body portion 74 is formed of light transmissive material similar to that of the cover 18 described above with respect to FIGS. 3, 4A-4D, 5, 6, 7A-7B, 8A-8D, 9A-9B, and 11A-11B. In some embodiments, the inner body portion 74 is formed from a soft, resilient material, such as silicone, which deforms when the device is attached to the body of a subject. However, various types of light transmissive materials may be utilized, without limitation.

A layer of cladding material 21 is applied to (or near) the outer surface 74a of the inner body portion 74 and a layer of cladding material 21 is applied to (or near) the inner surface 74b of the inner body portion 74, as illustrated, to define a light-guiding region 19. As such, the inner body portion 74 serves as a light guide that delivers light from the optical emitter 24 to the body of a subject at one or more predetermined locations and that collects light from the body and delivers the collected light to the optical detectors 26, 26'. In some embodiments, the cladding material 21 may be embedded within the inner body portion 74 adjacent to the outer surface 74a and inner surface 74b. In some embodiments, the outer body portion 72 may serve as a cladding layer adjacent to the inner body portion outer surface 74a.

In the illustrated embodiment, windows 74w are formed in the cladding material 21 and serve as light-guiding interfaces to the body of a subject. There may be any number of these windows, as may be required for sufficient optical coupling, and the windows 74w may include lenses such as those described above (e.g., lens 18L illustrated in FIG. 6), to focus light emitted by the optical emitter 24 onto one or more portions of the body of a subject and/or to focus collected light on the light detectors 26, 26'. Similarly, the windows 74w may include optical filters to selectively pass one or more optical wavelengths and reflect and/or absorb other optical wavelengths.

In the illustrated embodiment, the light-guiding region 19 includes a light blocking member 80 that isolates light emitter 24 and light detector 26 from each other. In some embodiments, multiple light emitters 24 may be utilized. For example, light emitters of different wavelengths may be utilized. In some embodiments, multiple light detectors may be utilized that are configured to measure light at different wavelengths (e.g., light detectors 26 and 26' may be configured to measure light at different wavelengths).

The illustrated monitoring device 70' may be removably attached to the body of a subject via adhesive on one or more portions of the device 70'. In some embodiments, adhesive may be on the inner body portion 74. In embodiments where the outer body portion is utilized, the adhesive may be on the outer body portion 74. In some embodiments, the illustrated device 70' may be removably attached to the body of a subject via tape or other known devices.

Referring now to FIGS. 24A-24B, 25A-25B, and 34-40, headsets 10 that utilize one or more light guides 119 that are optically coupled with (i.e., in optical communication with) one or more optical emitters and/or optical detectors, according to various embodiments of the present invention, are illustrated. Each illustrated headset 10 includes a housing 14 that is configured to be supported within an ear of a person, and may also enclose and protect various electronic components mounted to a base 50 (FIGS. 26-29) therewithin, as described above. For example, as described above, a base 50 may include any configuration and combination of one or more printed circuit boards, electrical connectors, processors, speakers, optical emitters and optical detectors. As such, each of the illustrated headsets 10 of FIGS. 24A-24B, 25A-25B and 34-40 may include at least one optical emitter 24 and at least one optical detector 26 disposed within the housing 14. However, as described below, one or more optical emitters and/or one or more optical detectors may be remotely located from the housing 14. As described above, each optical detector 26 may be a photodiode, photodetector, phototransistor, thyristor, solid state device, optical chipset, or the like. The optical emitter 24 may be a light-emitting diode (LED), laser diode (LD), compact incandescent bulb, micro-plasma emitter, IR blackbody source, or the like.

In the embodiments of FIGS. 24A-24B and 25A-25B, the distal end portion 119a of each of the light guides 119 extends outwardly from the housing 14. However, in other embodiments of the present invention, the distal end portion 119a of one or both light guides 119 may be substantially flush with the housing 14 or may even be recessed within the housing 14. The distal end 119a of each light guide 119 has an exposed end surface 119c that is configured to engage (or be positioned adjacent) a portion of an ear of a subject.

Figure 24A:
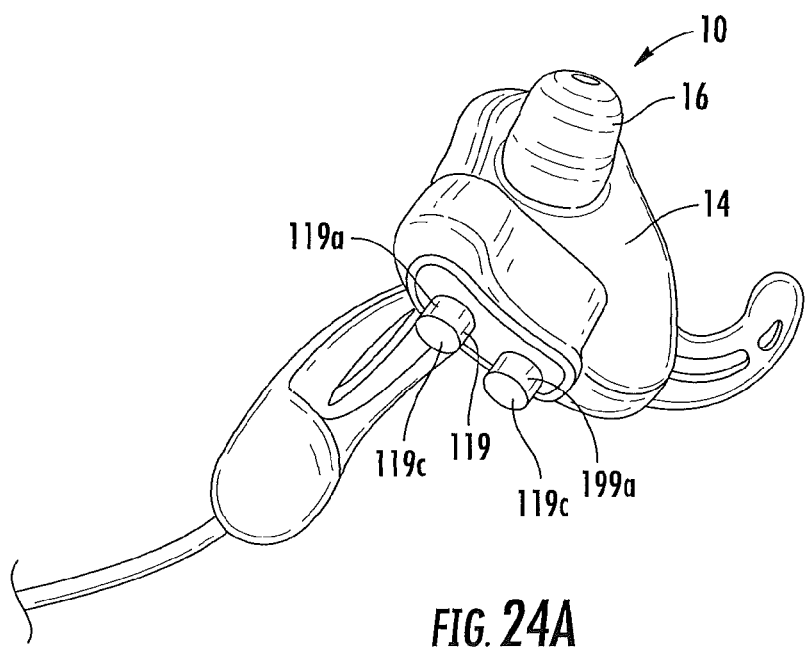
FIGS. 24A and 24B are perspective views of a headset having light guides extending from a housing thereof, according to some embodiments of the present invention, and wherein the light guides are in optical communication with an optical emitter and optical detector.
Figure 24B:
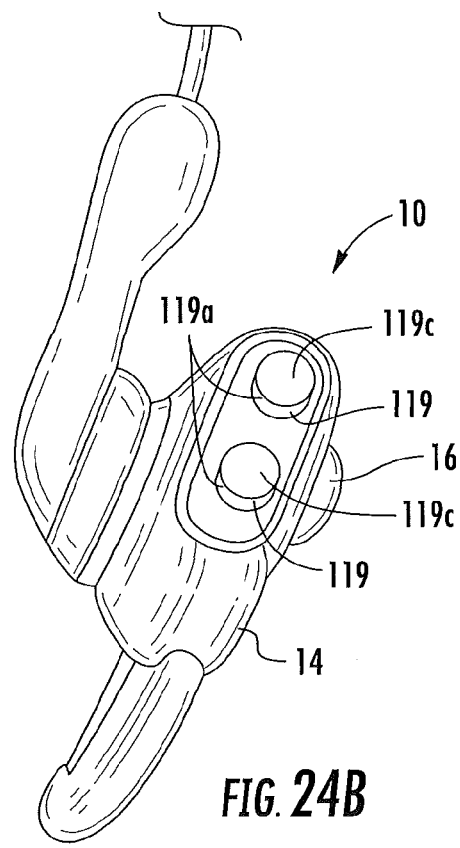
Figure 25A:
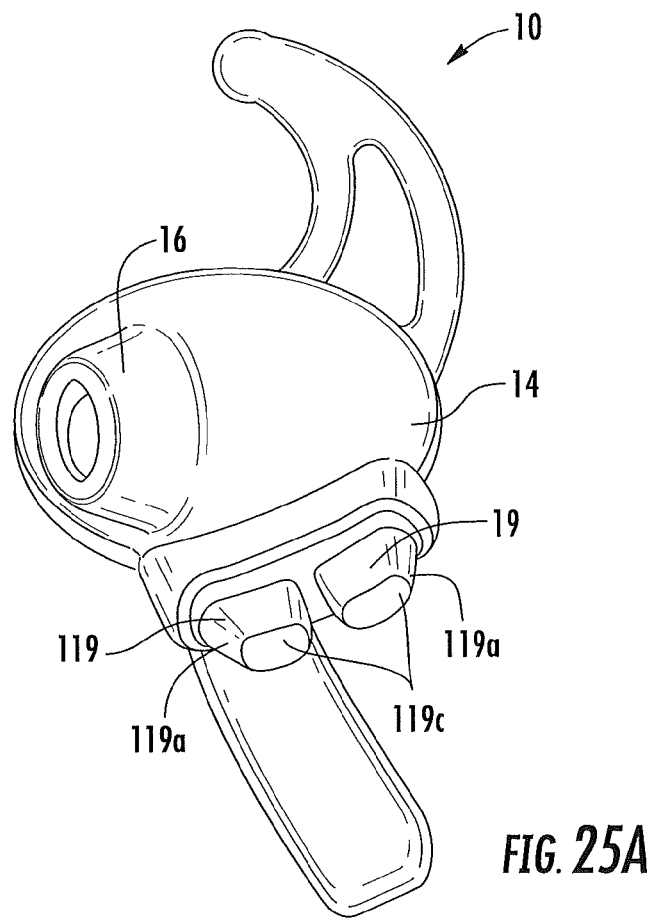
FIGS. 25A and 25B are perspective views of a headset having light guides extending from a housing thereof, according to some embodiments of the present invention, and wherein the light guides are in optical communication with an optical emitter and optical detector.
Figure 25B:
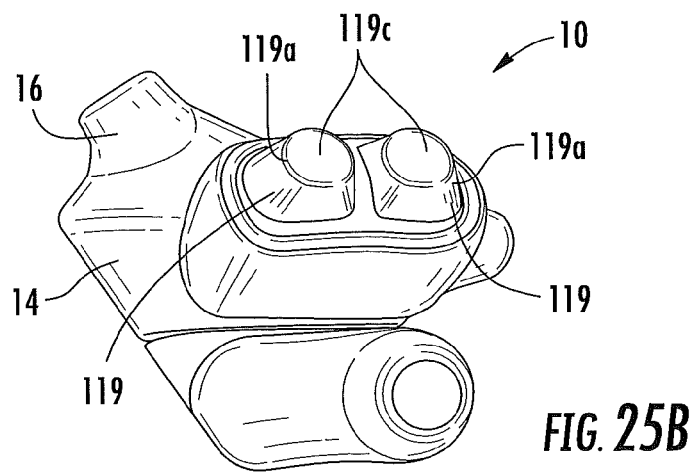
Figure 31:
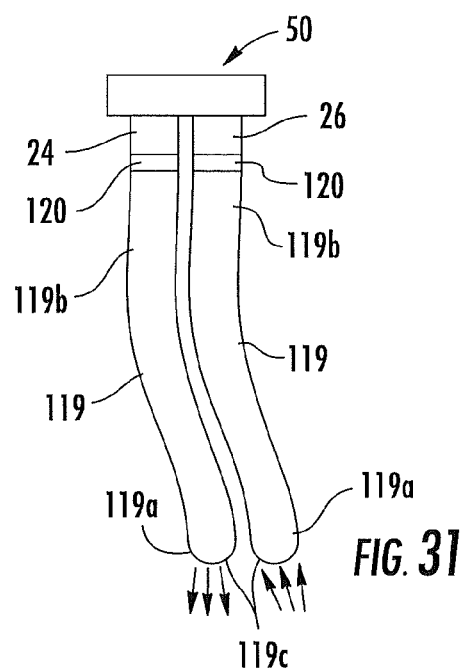
FIG. 31 illustrates elongated light guides that may be utilized with headsets and sensor modules, according to some embodiments of the present invention, such that an optical emitter and/or optical detector can be located remotely from the housing of a headset or sensor module.

The exposed surface 119c is shown with a flat surface in FIGS. 24A-24B and as a curve or rounded surface in FIG. 31 to demonstrate that light guides according to embodiments of the present invention may be shaped in a variety of ways to couple light to and from the body. For example, a rounded surface may improve light collection from a wider angle and a flat surface may narrow the field of view of the light guide. In some cases, a wider field of view may be important to measure more light from a broader range along the body, but in other cases, a narrower view may be important to focus the field of view on a specific region of the body. For example, a light guide 119 with a flat-faced surface 119c within the earbud 10 of FIGS. 24A-24B may focus the field of view to the region between the anti-tragus and concha of the ear. This region of the ear has been found by Applicants to contain a sufficient blood flow signal for photoplethysmography (PPG) while also being a region that is less prone to motion artifacts from chewing, talking, walking, running, or exercising. Less motion artifacts may result in less optical scatter from motion and hence result in less noise in the optical signal from the detector 26. A less noisy optical signal may result in a cleaner PPG signal upon analog or digital filtering of the optical signal. In contrast, a rounded distal end of a light guide as with the surface 119c of FIG. 31 may capture a greater PPG signal but an even greater amount of motion artifact related optical scatter. Detailed novel methods of filtering optical signals from the optical detector 26 are disclosed in co-owned, co-pending U.S. Patent Application Publication No. 2012/0197093, and co-owned, co-pending PCT Application No. PCT/US12/48079, which are incorporated herein by reference in their entireties.

As used herein, the term "engage" is intended to mean that the distal end surface 119c may contact the skin of a person or may be closely adjacent the skin of a person, such as within a hundred microns to 3 or more millimeters away from the person, for example.

An opposite proximal end 119b of each light guide 119 is in optical communication with a respective optical emitter 24 and optical detector 26. As such, a respective light guide 119 is configured to deliver light from an optical emitter 24 into an ear region of the subject via the distal end exposed surface 119c, and a respective light guide 119 is configured to collect light from an ear region of the subject via the distal end exposed surface 119c and deliver collected light to the optical detector 26.

Figure 34:
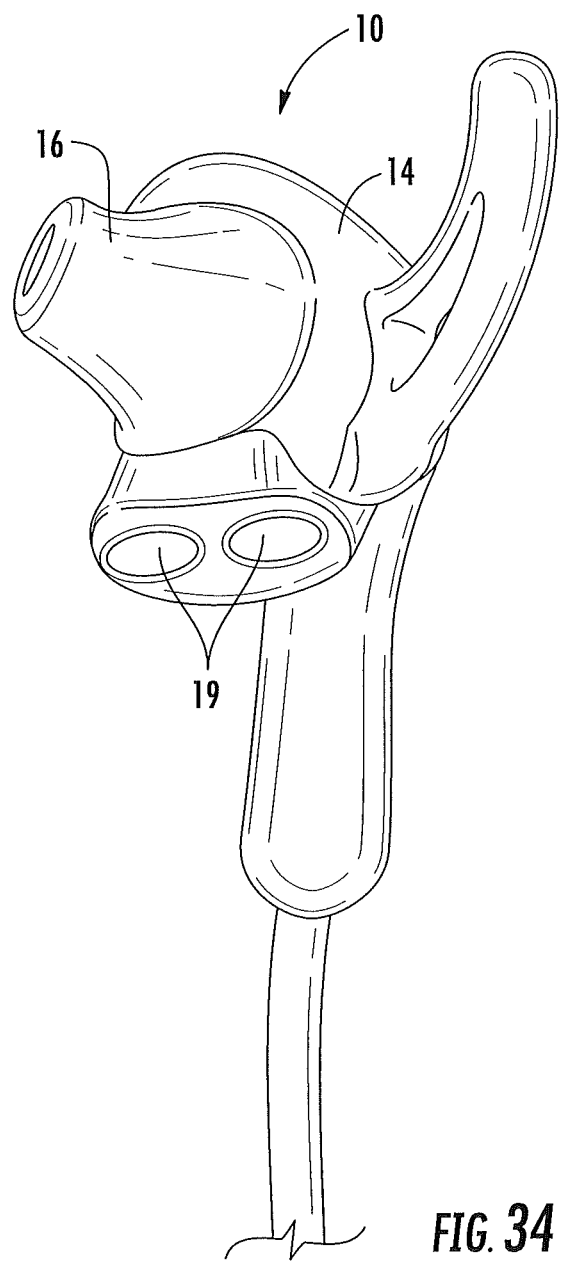
FIG. 34 is a perspective view of a headset having light guides, according to some embodiments of the present invention, and wherein the light guides are in optical communication with an optical emitter and optical detector.

In the illustrated embodiment of FIG. 34, the distal ends 119a of each light guide 119 do not extend from the housing 14. Instead, the distal ends 119a of each light guide 119 are substantially flush with the housing 14. In some embodiments, one or both of the distal ends 119a of the light guides 119 of FIG. 34 may be recessed within the housing 14. A benefit of recessing the light guides may be to further narrow the field of view or to improve the comfort of the headset 10 worn within the ear, as may be desired for some applications.

In the illustrated embodiment of FIGS. 24A-24B, the light guides 119 have an elongated, generally cylindrical configuration. In the illustrated embodiment of FIGS. 25A-25B, the light guides 119 have a non-cylindrical, generally tapered configuration. In the embodiment of FIG. 34, the light guides 119 have a generally oval cross-sectional configuration. However, embodiments of the present invention are not limited to the illustrated configuration or shape of the light guides 119 of FIGS. 24A-24B, 25A-25B and 34-40. Light guides 119 according to embodiments of the present invention may have various shapes, configurations, lengths, etc., without limitation. A benefit of a non-cylindrical or square light guide is that it may facilitate a more compact headset design.

Each light guide 119 in the various embodiments illustrated and described herein may be formed from various types of light transmissive material, typically with a refractive index of at least one (1). In some embodiments, a light guide 119 may be formed from an elastomeric light transmissive material. In other embodiments, a light guide 119 may be formed from a substantially rigid light transmissive material. In embodiments of the present invention where a headset or monitoring device includes a plurality of light guides 119, some of the light guides may be formed from an elastomeric light transmissive material, and some may be formed from a substantially rigid light transmissive material. Light guides according to some embodiments of the present invention may comprise one or more optical fibers. Exemplary light guide materials include, but are not limited to, polycarbonate, acrylic, silicone, and polyurethane.

Light guides 119, according to some embodiments of the present invention, may comprise optical filtering material, also. For example, a light-guide may comprise a material having an optically filtering dye or a material which inherently filters one or more wavelengths of light. For example, a light-absorptive dye, many of which are well-known in the art, may be integrated within or coated on top a polycarbonate or acrylic sheet. Similarly, a light-absorptive dye may be integrated within a resin which may then be molded into one or more light guides. A few non-limiting examples of an inherently filtering material includes sapphire, which absorbs some infrared (IR) wavelengths, or glass, which absorbs some ultraviolet (UV) wavelengths. However, various types of filtering material may be utilized, without limitation.

Figure 30:
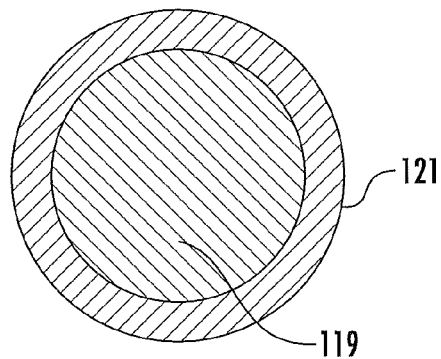
FIG. 30 is an enlarged cross-sectional view of a light guide with a layer of cladding material surrounding the light guide, according to some embodiments of the present invention.

In some embodiments, a light guide 119 may be surrounded or partially surrounded by a cladding material 121 (FIG. 30) that is configured to block light from an external source from entering the light guide 119 and/or at least partially confine light within the light guide 119. The cladding material 121 may be a light blocking material and/or a light reflective material. For example, the cladding material 121 may be a dark (e.g., black, etc.) or silver (or other reflective color) coating, or a texturized light-scattering material on one or more portions of the surface of the light guide 119.

Figure 26:
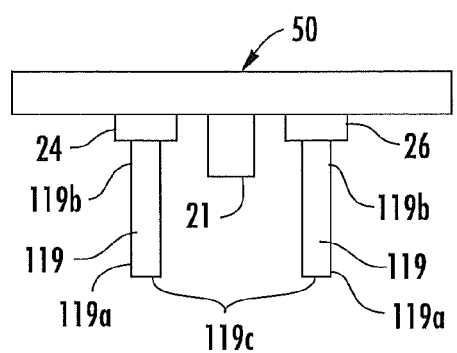
FIGS. 26-29 are illustrate various light guide configurations that may be utilized within headsets and sensor modules, according to some embodiments of the present invention.
Figure 27:
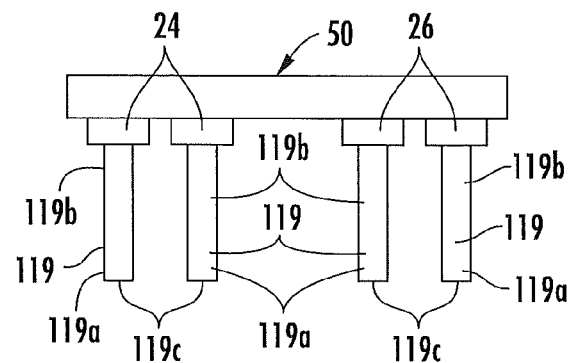
Figure 28:
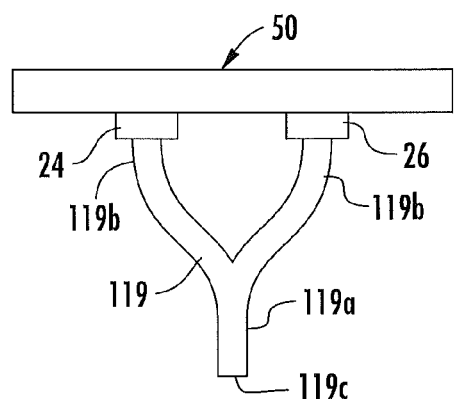
Figure 29:
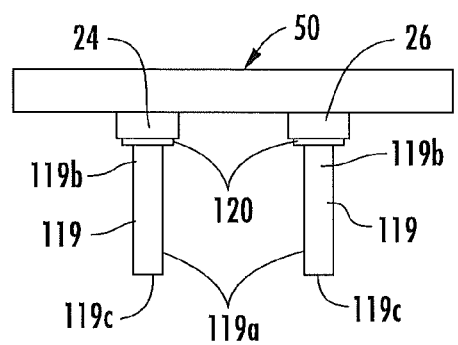

FIGS. 26-29 illustrate various light guide configurations that may be utilized within headsets and wearable sensor modules (e.g., sensor modules that can be attached to earlobes, fingers, wrists, ankles, toes, other digits, other skin regions, etc.), according to some embodiments of the present invention. For example, when used in conjunction with Applicants' signal extraction technology, these sensor modules may function well when embedded within a wrist strap, wrist watch, ankle bracelet, armband, chest strap, and other form-factors that can engage the sensor module with the skin. Although the light guides 119 in FIGS. 26, 27 and 29 are illustrated as having the same length, it is understood that embodiments of the present invention are not limited to light guides 119 having the same length.

In FIG. 26, an optical emitter 24 and optical detector 26 are attached to a base 50 and light blocking material 21 is positioned between the optical emitter 24 and detector 26 such that the optical emitter 24 and detector 26 are not in direct optical communication with each other. In some embodiments, the light blocking material 21 may completely block light from the optical emitter from directly reaching the optical detector 26. In other embodiments, the light blocking material 21 may partially block light from the optical emitter from directly reaching the optical detector 26.

As illustrated in FIG. 26, a respective light guide 119 is in optical communication with the optical emitter 24 and optical detector 26. However, in other embodiments, a plurality of light guides 119 may be in optical communication with the light emitter 24 and/or light detector 26. It should be noted that the free end 119c of the light guide 119 may branch out to two or more "legs" that may be used to couple with many different parts of the body, such as multiple parts of the ear. Monitoring multiple regions of the ear may be beneficial as described in co-owned and copending U.S. Patent Application Publication No. 2010/0217098, which is incorporated herein by reference in its entirety.

As illustrated in FIG. 27, a headset or sensor module may include a plurality of optical emitters 24 and/or optical detectors 26 with a respective light guide in optical communication therewith. It should be noted that the light guides 119 may be used to couple with many different parts of the body, such as multiple parts of the ear.

As illustrated in FIG. 28, a single light guide 119 may be in optical communication with an optical emitter 24 and with an optical detector 26.

As illustrated in FIG. 29, optical coupling material 120 may be applied to one or both of the optical emitter 24 and optical detector 26 of a headset or sensor module. A light guide 119 is in optical communication with the optical emitter 24 and optical detector 26 via the optical coupling material 120. The optical coupling material 120 may comprise a material that effectively couples light from the optical emitter 24 to the light guide 119 or from the light guide 119 to the optical detector 26. Examples of suitable materials include, but are not limited to, glue, tape, resin, gel, filler material, molded material or the like. A few non-limiting examples of a molded material may include, but are not limited to, silicone, plastic, polymer, or polyurethane part that is form-fitted to matingly engage the light guide and the emitter and/or detector. A benefit of molded, form-fitted optical coupling is that it may be routinely attached/detached due to the non-permanent interface. This may be useful for the case where a light guide 119 may need to be routinely attached/detached from an emitter 24 and/or detector 26. Two attractive properties of suitable optical coupling materials may include: 1) a refractive index that matches or closely matches that of the emitter, detector, or light guide and 2) providing a solid interface between the coupled elements without an air gap in between.

Figure 32:
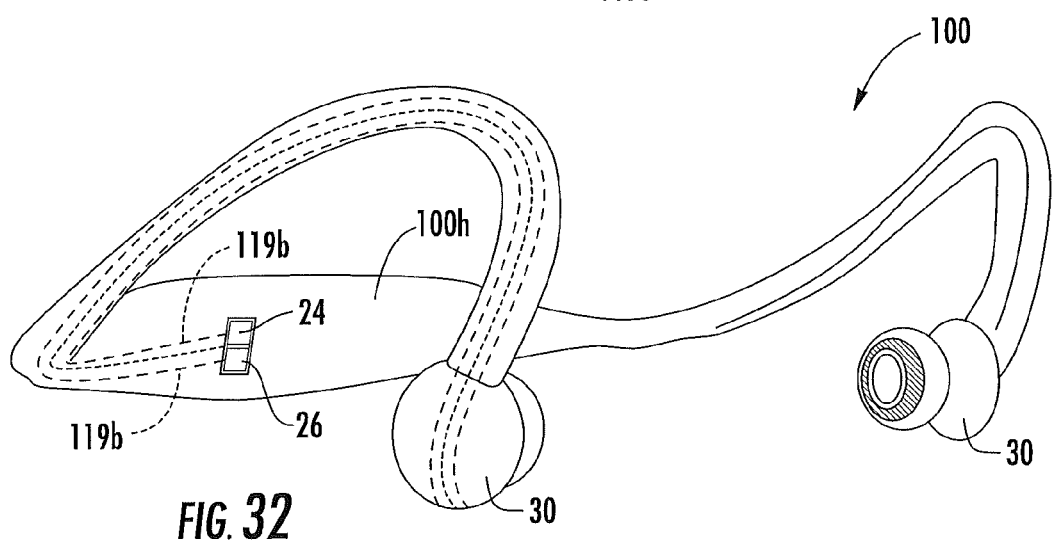
FIG. 32 is a perspective view of a stereo headset wherein an optical emitter and optical detector are located remotely from the earbuds and wherein light guides extend from the optical emitter and optical detector to an earbud, according to some embodiments of the present invention.

In some embodiments of the present invention, such as illustrated in FIGS. 24A-24B and 25A-25B, an optical emitter 24 and optical detector 26 are attached to or disposed within the housing 14. However, in other embodiments of the present invention, an optical emitter 24 and/or optical detector 26 can be located remotely from the housing 14. For example, as illustrated in FIG. 32, the optical emitter 24 and optical detector 26 may be located on a headband or other structure that is a part of a headset. In the illustrated embodiment of FIG. 32, the headset 100 is a stereo headset having a pair of earbuds 30. An optical emitter 24 and optical detector 26 are located on the headband 100h of the headset 100. In some embodiments with wired headphones, the emitter and/or detector may be located on a "medallion" or a mobile device (such as a smartphone) itself, with the associated light guide(s) running in between the headphone and the medallion or mobile device.

Figure 33:
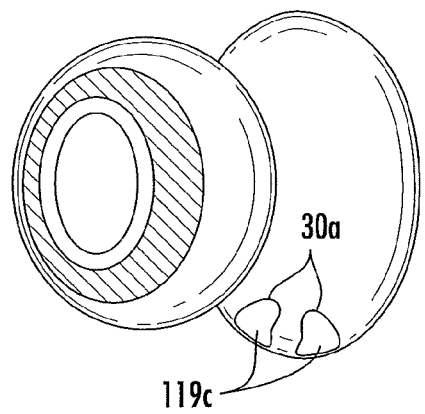
FIG. 33 is an enlarged perspective view of an earbud of the headset of FIG. 32 and illustrating the exposed distal ends of the light guides of FIG. 32.

A pair of elongated light guides 119, such as illustrated in FIG. 31, are in optical communication with the optical emitter 24 and optical detector 26 via proximal end portions 119b and extend from the optical emitter 24 and optical detector 26 to an earbud 30. The earbud 30 includes a pair of apertures 30a formed therethrough. Each light guide distal end is positioned within a respective earbud aperture 30a such an exposed end surface 119c thereof is configured to engage (or be positioned adjacent) a portion of an ear of a subject. As such, the light guide 119 in optical communication with the optical emitter 24 can deliver light from the optical emitter 24 into an ear region of the subject, and the light guide 119 in optical communication with the optical detector 26 can collect light from the ear region of the subject and deliver collected light to the optical detector 26. It should be noted that the distal free end surface 119c of the light guide 119 may comprise a variety of shapes, as discussed previously, more than exemplarily shown in FIG. 33.

The optical emitter 24 and optical detector 26 may be embedded within the headband 100h (also referred to as a "back band" as this may typically be worn behind the head), or may be located external to the headband 100h. In addition, the elongated light guides 119 in communication with the optical emitter 24 and optical detector 26 may be embedded within the headband 100h. However, in some embodiments of the present invention, the elongated light guides 119 may be external or at least partially external to the headband 110h.

Though many of the drawings herein show emitters and detectors in only one earbud, it should be understood that the emitters and detectors may be in multiple earbuds, left and right, for use in biometric monitoring. Certain benefits may be realized by incorporating light guides from the headband to both earbuds. For example, having emitters and detectors in multiple earbuds may enable the ability to measure the transit time between blood pulses on the right and left sides of the head, and this measurement may be used to estimate the blood pressure of the person. For example, the blood moving from the carotid artery on the right of the head and moving to the left of the head may be modulated in part by the blood pressure, and thus by measuring the time difference between right and left blood pulses, and by integrating this measurement into a formula relating pulse transit time and blood pressure, potentially further including a relationship for arterial stiffness, a method of determining blood pressure may be implemented. Additionally, the difference between the intensity of the pulsatile blood flow signals, namely the difference in amplitude of the AC blood flow pulses, between the right and left sides of the head may be directly proportional to the blood pressure of the person wearing the headset. A suitable stereo headset configuration for providing this type of functionality may comprise a light guiding method as shown in FIG. 27, with a plurality of emitters and detectors.

Figure 35:
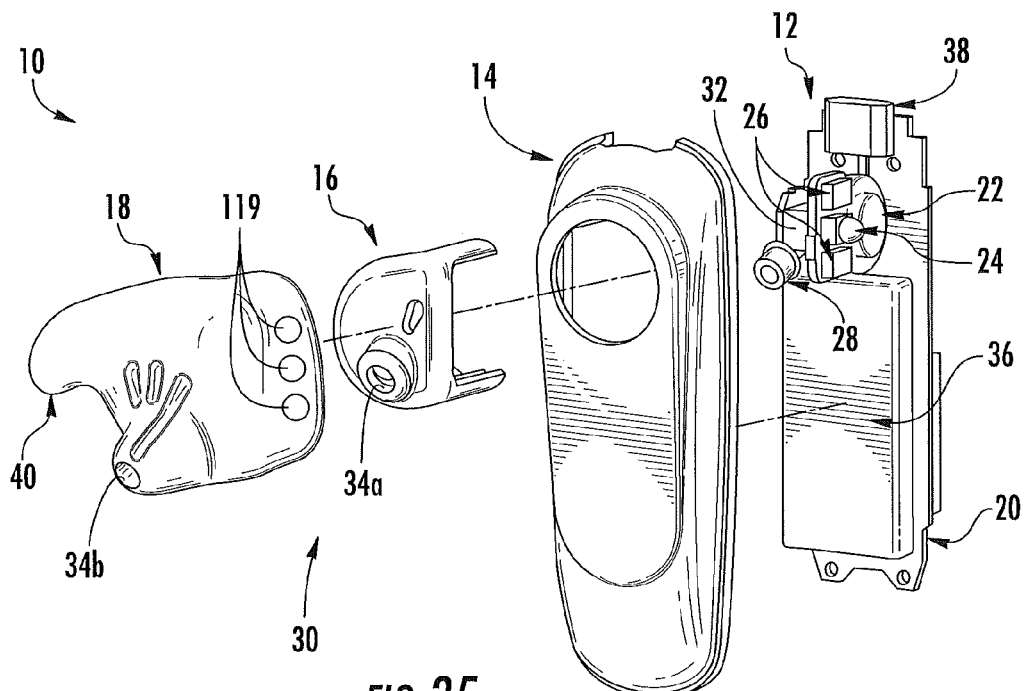
FIG. 35 is an exploded perspective view of a headset with an earbud housing having a plurality of light guides associated therewith, according to some embodiments of the present invention.
Figure 36:
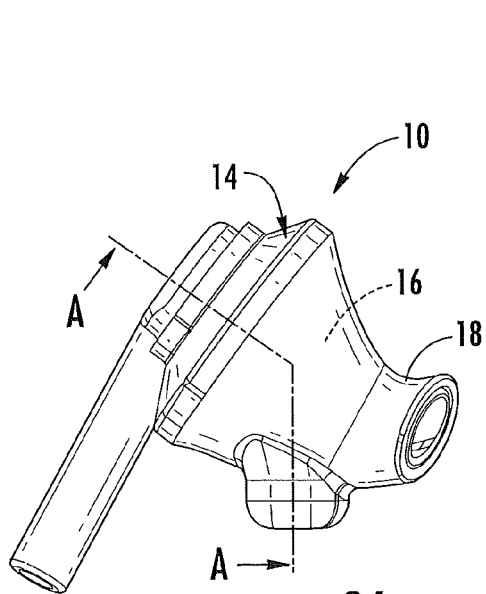
FIG. 36 is a perspective view of a headset with an earbud housing having light guides associated therewith, according to some embodiments of the present invention.
Figure 37:
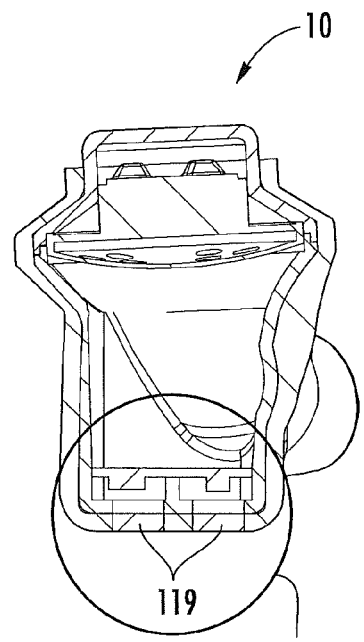
FIG. 37 is a cross sectional view of the headset of FIG. 36 taken along lines A-A.

FIG. 35 illustrates the headset 10 of FIG. 1 with light guides 119 in the earbud housing cover 18, according to some embodiments of the present invention. Each light guide 119 is configured to be in optical communication with a respective one of the optical emitter 24 and optical detectors 26. In this embodiment, the earbud housing cover 18 may be substantially opaque. As such, the only light transmissive paths are via the light guides 119. However, embodiments of the present invention represented by FIG. 35 do not require that the housing cover 18 be opaque.

Figure 40:
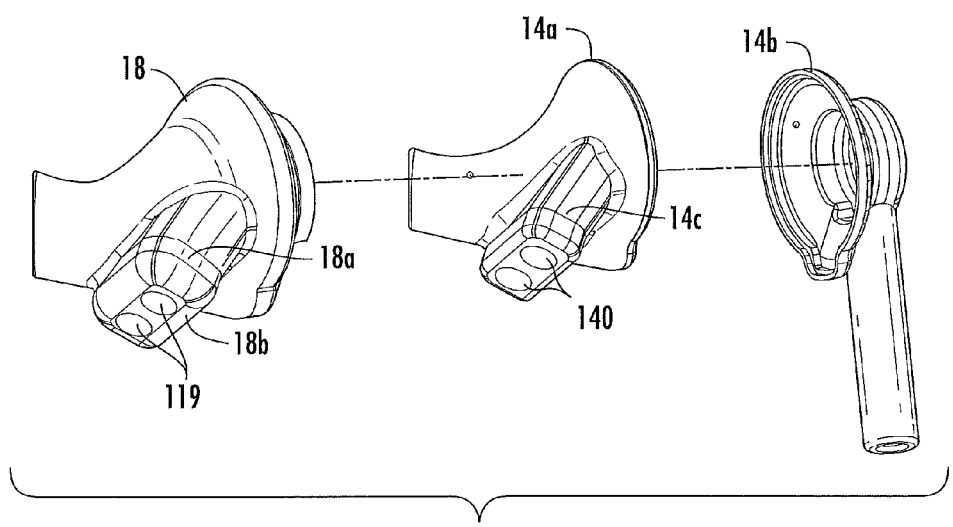
FIG. 40 is an exploded perspective view of the headset of FIG. 39.

FIGS. 36-40 illustrate a headset 10 incorporating light guides 119 according to other embodiments of the present invention. The headset housing 14 includes an opaque front housing portion 14a (FIG. 40) and an opaque rear housing portion 14b (FIG. 40). A removable cover 18 is configured to be attached to and matingly engage the front housing portion 14a. The cover 18 can be provided in various sizes, each adapted to the shape and size of an ear of a subject. For example, covers 18 may come in large, medium, and small sizes, etc. The cover 18 may be formed from a soft or elastomeric material. Examples of suitable soft or elastomeric materials may include, but are not limited to, silicone, rubber, polymer-based materials, latex, lower durometer plastics, and the like.

Figure 38:
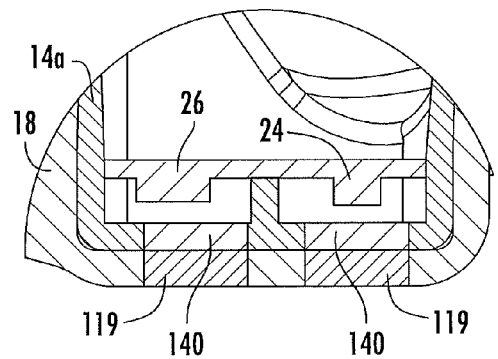
FIG. 38 is an enlarged partial view of the headset of FIG. 37.
Figure 39:
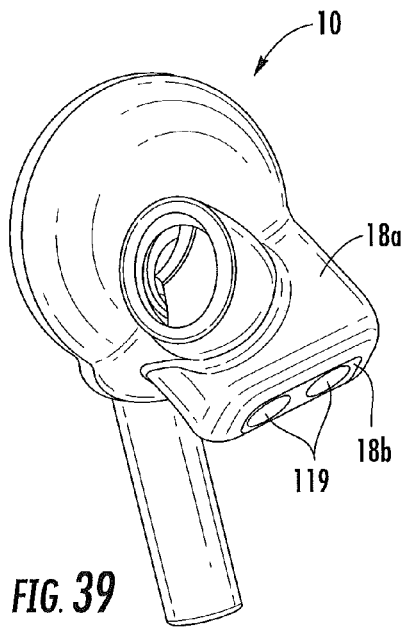
FIG. 39 is a perspective view of a headset with an earbud housing having light guides associated therewith, according to some embodiments of the present invention.

The front housing portion 14 a includes a portion 14c that has a pair of filter lenses 140 integral therewith. The cover 18 has a corresponding portion 18a that includes a pair of light guides 119 integral therewith, as illustrated. The light guides 119 are substantially flush with an end surface 18b of portion 18a in the illustrated embodiment. When the cover 18 is installed on the front housing portion 14a, the light guides 119 are in alignment (i.e., optical communication) with the filter lenses 140, as illustrated in FIG. 38.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A method of monitoring a subject via a sensor module, wherein the sensor module includes at least one optical emitter and at least one optical detector, a first light guide having a proximal end optically coupled to the at least one optical emitter and an opposite distal end with a free end surface, and a second light guide having a proximal end optically coupled to the at least one optical detector and an opposite distal end with a free end surface, the method comprising:
   attaching the sensor module to a body of the subject such that the respective distal end free end surfaces of the first and second light guides engage respective portions of the body of the subject;
   delivering light from the at least one optical emitter directly into the body of the subject via the distal end free end surface of the first light guide; and
   collecting light directly from the body of the subject via the distal end free end surface of the second light guide.

2. The method of claim 1, wherein the sensor module includes at least one motion sensor, and further comprising sensing motion information from the subject via the at least one motion sensor.

3. The method of claim 2, wherein the sensor module includes at least one signal processor, and further comprising removing, via the at least one signal processor, motion artifacts from signals produced by the at least one optical detector in response to signals produced by the at least one motion sensor.

4. The method of claim 1, wherein the sensor module includes at least one signal processor, and further comprising processing, via the at least one signal processor, signals produced by the at least one optical detector to detect and/or measure physiological information about the subject.

5. The method of claim 1, wherein the sensor module includes at least one signal processor and at least one motion sensor, and further comprising processing, via the at least one signal processor, signals produced by the at least one optical detector and signals produced by the at least one motion sensor to determine subject heart rate and respiration rate.

6. The method of claim 1, wherein the sensor module is included within an earbud of a headset, wherein attaching the sensor module to a body of the subject comprises positioning the earbud within an ear of the subject such that the respective distal end free end surfaces of the first and second light guides engage respective portions of the ear, wherein delivering light from the at least one optical emitter directly into the body of the subject via the distal end free end surface of the first light guide comprises delivering light from the optical emitter into an ear region, and wherein collecting light from the body of the subject via the distal end free end surface of the second light guide comprises collecting light from the ear region.

7. The method of claim 6, wherein the ear region is between the anti tragus and concha of the ear.

8. The method of claim 1, wherein the sensor module includes a signal processor, and further comprising executing an adaptive filter algorithm via the signal processor to remove noise from signals produced by the at least one optical emitter.

9. A method of monitoring a subject via a headset, wherein the headset includes at least one optical emitter, at least one optical detector, a first light guide having a proximal end optically coupled to the at least one optical emitter and an opposite distal end, a second light guide having a proximal end optically coupled to the at least one optical detector and an opposite distal end, and a housing configured to be positioned within an ear of a subject, the method comprising:
   positioning the housing within the ear of the subject such that the housing is supported by the ear and such that the first and second light guide distal ends are not located within the ear canal;
   delivering light from the at least one optical emitter into the ear in a first direction away from the ear canal via the first light guide distal end; and collecting light from the ear in a second direction away from the ear canal via the second light guide distal end.

10. The method of claim 9, wherein delivering light from the at least one optical emitter into the ear comprises delivering light to a region of the ear between the anti tragus and concha.

11. The method of claim 9, wherein the first and second directions are substantially parallel.

12. The method of claim 9, wherein the headset includes at least one motion sensor, and further comprising sensing motion information from the subject via the at least one motion sensor.

13. The method of claim 12, wherein the headset includes at least one signal processor, and further comprising removing, via the at least one signal processor, motion artifacts from signals produced by the at least one optical detector in response to signals produced by the at least one motion sensor.

14. The method of claim 9, wherein the headset includes at least one signal processor, and further comprising processing, via the at least one signal processor, signals produced by the at least one optical detector to detect and/or measure physiological information about the subject.

15. The method of claim 9, wherein the headset includes at least one signal processor and at least one motion sensor, and further comprising processing, via the at least one signal processor, signals produced by the at least one optical detector and signals produced by the at least one motion sensor to determine subject heart rate and respiration rate.

16. The method of claim 9, wherein the sensor module includes a signal processor, and further comprising executing an adaptive filter algorithm via the signal processor to remove noise from signals produced by the at least one optical emitter.

17. A method of monitoring a subject via a headset, wherein the headset includes at least one optical emitter, at least one optical detector, at least one signal processor, a first light guide having a proximal end optically coupled to the at least one optical emitter and an opposite distal end with a free end surface, a second light guide having a proximal end optically coupled to the at least one optical detector and an opposite distal end with a free end surface, and a housing configured to be positioned within an ear of a subject, the ear having an anti tragus and a concha, the method comprising:
  positioning the housing within the ear of the subject such that the housing is supported by the ear and such that the respective distal end free end surfaces of the first and second light guides engage respective portions of the ear between the anti tragus and concha;
  delivering light from the at least one optical emitter into a region of the ear between the anti tragus and concha via the distal end free end surface of the first light guide;
  collecting light from the region of the ear between the anti tragus and concha via the distal end free end surface of the second light guide; and
  processing, via the at least one signal processor, signals produced by the at least one optical detector to determine subject heart rate and respiration rate.

18. The method of claim 17:
wherein
processing the signals produced by the at least one optical detector to determine subject heart rate and respiration rate comprises utilizing at least one digital filter and at least one peak finding algorithm.

* * * * *